(12) United States Patent
Commandeur et al.

(10) Patent No.: US 10,190,128 B2
(45) Date of Patent: Jan. 29, 2019

(54) KITS COMPRISING PLUS-SENSE SINGLE STRANDED RNA VIRAL VECTORS AND METHODS FOR PRODUCING POLYPEPTIDES USING THE KITS

(71) Applicants: Fraunhofer-Gesellschaft zur Förderung der angewandten Forschung e.V., München (DE); RHEINISCH-WESTFÄLISCHE TECHNISCHE HOCHSCHULE AACHEN, Aachen (DE)

(72) Inventors: Ulrich Commandeur, Aachen (DE); Christina Dickmeis, Aachen (DE); Rainer Fischer, Aachen (DE)

(73) Assignees: Fraunhofer-Gesellschaft zur Förderung der angewandten Forschung e.V., München (DE); Rheinisch-Westfälische Technische Hochschule Aachen, Aachen (DE)

(*) Notice: Subject to any disclaimer, the term of this patent is extended or adjusted under 35 U.S.C. 154(b) by 235 days.

(21) Appl. No.: 14/764,112

(22) PCT Filed: Mar. 21, 2014

(86) PCT No.: PCT/EP2014/055730
§ 371 (c)(1),
(2) Date: Jul. 28, 2015

(87) PCT Pub. No.: WO2014/147235
PCT Pub. Date: Sep. 25, 2014

(65) Prior Publication Data
US 2016/0145635 A1 May 26, 2016

(30) Foreign Application Priority Data
Mar. 22, 2013 (EP) .................................. 13160627

(51) Int. Cl.
*C12N 15/82* (2006.01)

(52) U.S. Cl.
CPC .............. *C12N 15/8242* (2013.01); *C12N 2770/00043* (2013.01); *C12N 2770/40043* (2013.01)

(58) Field of Classification Search
None
See application file for complete search history.

(56) References Cited

U.S. PATENT DOCUMENTS

| | | | |
|---|---|---|---|
| 4,940,838 A | 7/1990 | Schilperoort et al. |
| 5,100,792 A | 3/1992 | Sanford et al. |
| 5,464,763 A | 11/1995 | Schilperoort et al. |
| 5,591,616 A | 1/1997 | Hiei et al. |
| 2009/0111145 A1 | 4/2009 | Giritch et al. |
| 2010/0071085 A1 | 3/2010 | Lindbo |

FOREIGN PATENT DOCUMENTS

| | | | |
|---|---|---|---|
| EP | 175966 B1 | 1/1990 | |
| EP | 0290395 B1 | 1/1994 | |
| EP | 0564595 B1 | 4/1995 | |
| EP | 0434616 B1 | 11/1995 | |
| EP | 0444882 B1 | 5/2000 | |
| EP | 1686176 A1 * | 8/2006 | ............ C07K 14/59 |
| EP | 1686176 A1 | 8/2006 | |
| EP | 2418283 A1 | 2/2012 | |
| JP | 2002-537842 A | 11/2002 | |
| JP | 2003-517280 A | 5/2003 | |
| WO | WO-87/06614 A1 | 11/1987 | |
| WO | WO-92/09696 A1 | 6/1992 | |
| WO | WO-94/00583 A1 | 1/1994 | |
| WO | WO-96/12027 A1 | 4/1996 | |
| WO | WO-00/46350 A1 | 8/2000 | |
| WO | WO-00/53780 A2 | 9/2000 | |
| WO | WO-03/020938 A2 | 3/2003 | |
| WO | WO-2004/070016 A2 | 8/2004 | |
| WO | WO-2008/028661 | 3/2008 | |
| WO | WO-2009/048354 A1 | 4/2009 | |

OTHER PUBLICATIONS

Giritch et al., "Rapid high-yield expression of full-size IgG antibodies in plants coinfected with noncompeting viral vectors," Proc Natl Acad Sci U S A. 103(40): 14701-6 (2006).
Roy et al., "A novel two-component Tobacco mosaic virus-based vector system for high-level expression of multiple therapeutic proteins including a human monoclonal antibody in plants," Virology. 405(1): 93-9 (2010).
Bazzini et al., "Tobacco mosaic virus (TMV) and potato virus X (PVX) coat proteins confer heterologous interference to PVX and TMV infection, respectively," J Gen Virol. 87(Pt 4):1005-12 (2006).
Fedorkin et al., "Complementation of the movement-deficient mutations in potato virus X: potyvirus coat protein mediates cell-to-cell trafficking of C-terminal truncation but not deletion mutant of potexvirus coat protein," Virology. 270(1):31-42 (2000).
Fischer et al., "Plant-based production of biopharmaceuticals," Curr Opin Plant Biol. 7(2):152-8 (2004).
Huang et al., "A DNA replicon system for rapid high-level production of virus-like particles in plants," available in PMC Jul. 1, 2010, published in final edited form as: Biotechnol Bioeng. 103(4):706-14 (2009) (16 pages).
International Preliminary Report on Patentability for International Application No. PCT/EP2014/055730, dated Oct. 1, 2015 (8 pages).
Julve et al., "A coat-independent superinfection exclusion rapidly imposed in Nicotiana benthamiana cells by tobacco mosaic virus is not prevented by depletion of the movement protein," Plant Mol Biol. 81(6):553-64 (2013).
Komarova et al., "New viral vector for efficient production of target proteins in plants," Biochemistry (Mosc). 71(8):846-50 (2006).

(Continued)

*Primary Examiner* — Elizabeth F McElwain
(74) *Attorney, Agent, or Firm* — Clark & Elbing LLP

(57) ABSTRACT

The present invention relates to kits comprising plus-sense single stranded RNA viral vectors, as well as mixtures of these vectors and uses thereof, and methods for producing in a plant, or plant tissue, or plant cell simultaneously two or more polypeptides using the kits and vectors.

33 Claims, 14 Drawing Sheets
Specification includes a Sequence Listing.

(56) References Cited

OTHER PUBLICATIONS

Komarova et al., "Transient expression systems for plant-derived biopharmaceuticals," Expert Rev Vaccines. 9(8):859-76 (2010).
Laemmli, "Cleavage of structural proteins during the assembly of the head of bacteriophage T4," Nature. 227(5259):680-5 (1970).
Larsen et al., "RNA viral vectors for improved Agrobacterium-mediated transient expression of heterologous proteins in Nicotiana benthamiana cell suspensions and hairy roots," BMC Biotechnol. 12(21): 11 pages (2012).
Lico et al., "The use of plants for the production of therapeutic human peptides," Plant Cell Rep. 31(3):439-51 (2012).
Maclean et al., "Optimization of human papillomavirus type 16 (HPV-16) L1 expression in plants: comparison of the suitability of different HPV-16 L1 gene variants and different cell-compartment localization," J Gen Virol. 88(Pt 5):1460-9 (2007).
Spitsin et al., "Expression of alfalfa mosaic virus coat protein in tobacco mosaic virus (TMV) deficient in the production of its native coat protein supports long-distance movement of a chimeric TMV," Proc Natl Acad Sci USA. 96(5):2549-53 (1999).
Tyulkina et al., "New viral vector for superproduction of epitopes of vaccine proteins in plants," Acta Naturae. 3(4):73-82 (2011).
Mendoza et al., "Expression of separate proteins in the same plant leaves and cells using two independent virus-based gene vectors," Front Plant Sci. 8:1808 (2017) (8 pages).
Hameed et al., "Detection of multiple potato viruses in the field suggests synergistic interactions among potato viruses in Pakistan," Plant Pathol J. 30(4):407-415 (2014).

\* cited by examiner

Figure 4

PVX-ΔCP-ORFx

| -PVX- RdRp | | TGB | ORFx |

Figure 5

PVX-ΔCP-ΔTGB-ORFx

| -PVX- RdRp | ORFx |

A)

B)

Figure 7

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: M13 universe primer

<400> SEQUENCE: 1
gttgtaaaac gacggccagt                                           20

<210> SEQ ID NO 2
<211> LENGTH: 22
<212> TYPE: DNA
<213> ORGANISM: Artificial Sequence
<220> FEATURE:
<223> OTHER INFORMATION: mCherry-ClaI primer

<400> SEQUENCE: 2
tagcatcgat atggtgagca ag                                        22

<210> SEQ ID NO 3
<211> LENGTH: 20
<212> TYPE: DNA
<213> ORGANISM: Artificial Sequence
<220> FEATURE:
<223> OTHER INFORMATION: PacI-GFP-TMV primer

<400> SEQUENCE: 3
tcattaatta aatggctagc                                           20

<210> SEQ ID NO 4
<211> LENGTH: 37
<212> TYPE: DNA
<213> ORGANISM: Artificial Sequence
<220> FEATURE:
<223> OTHER INFORMATION: SOE2-CPfw primer

<400> SEQUENCE: 4
agtacgtttt aatcaatatg tcagcaccag ctagcac                        37

<210> SEQ ID NO 5
<211> LENGTH: 37
<212> TYPE: DNA
<213> ORGANISM: Artificial Sequence
<220> FEATURE:
<223> OTHER INFORMATION: SOE2-CP-rv primer

<400> SEQUENCE: 5
tgctagctgg tgctgacata ttgattaaaa cgtactc                        37

<210> SEQ ID NO 6
<211> LENGTH: 26
<212> TYPE: DNA
<213> ORGANISM: Artificial Sequence
<220> FEATURE:
<223> OTHER INFORMATION: SOE2-CP-NotI-rv primer

<400> SEQUENCE: 6
aatagcggcc gctatggtgg tggtag                                    26

<210> SEQ ID NO 7
<211> LENGTH: 30
<212> TYPE: DNA
<213> ORGANISM: Artificial Sequence

```
<220> FEATURE:
<223> OTHER INFORMATION: SOE-TMVCP-fw primer

<400> SEQUENCE: 7
attgatactc gaaagatgcc ttatacaatc                                30

<210> SEQ ID NO 8
<211> LENGTH: 30
<212> TYPE: DNA
<213> ORGANISM: Artificial Sequence
<220> FEATURE:
<223> OTHER INFORMATION: SOE-TMVCP-rv primer

<400> SEQUENCE: 8
attgtataag gcatctttcg agtatcaatg                                30

<210> SEQ ID NO 9
<211> LENGTH: 31
<212> TYPE: DNA
<213> ORGANISM: Artificial Sequence
<220> FEATURE:
<223> OTHER INFORMATION: SOE-TMVCP2-fw primer

<400> SEQUENCE: 9
aactccggct acttaactac gtctacataa c                              31

<210> SEQ ID NO 10
<211> LENGTH: 25
<212> TYPE: DNA
<213> ORGANISM: Artificial Sequence
<220> FEATURE:
<223> OTHER INFORMATION: SOE-TMVCP2-rv primer

<400> SEQUENCE: 10
agacgtagtt aagtagccgg agttg                                     25

<210> SEQ ID NO 11
<211> LENGTH: 28
<212> TYPE: DNA
<213> ORGANISM: Artificial Sequence
<220> FEATURE:
<223> OTHER INFORMATION: 2ADelCPfw primer

<400> SEQUENCE: 11
aatccggata actacgtcta cataaccg                                  28
```

KITS COMPRISING PLUS-SENSE SINGLE STRANDED RNA VIRAL VECTORS AND METHODS FOR PRODUCING POLYPEPTIDES USING THE KITS

The present invention relates to kits comprising plus-sense single stranded RNA viral vectors, as well as mixtures of these vectors and uses thereof, and methods for producing in a plant, or plant tissue, or plant cell simultaneously two or more polypeptides using the kits and vectors.

Figure 1:
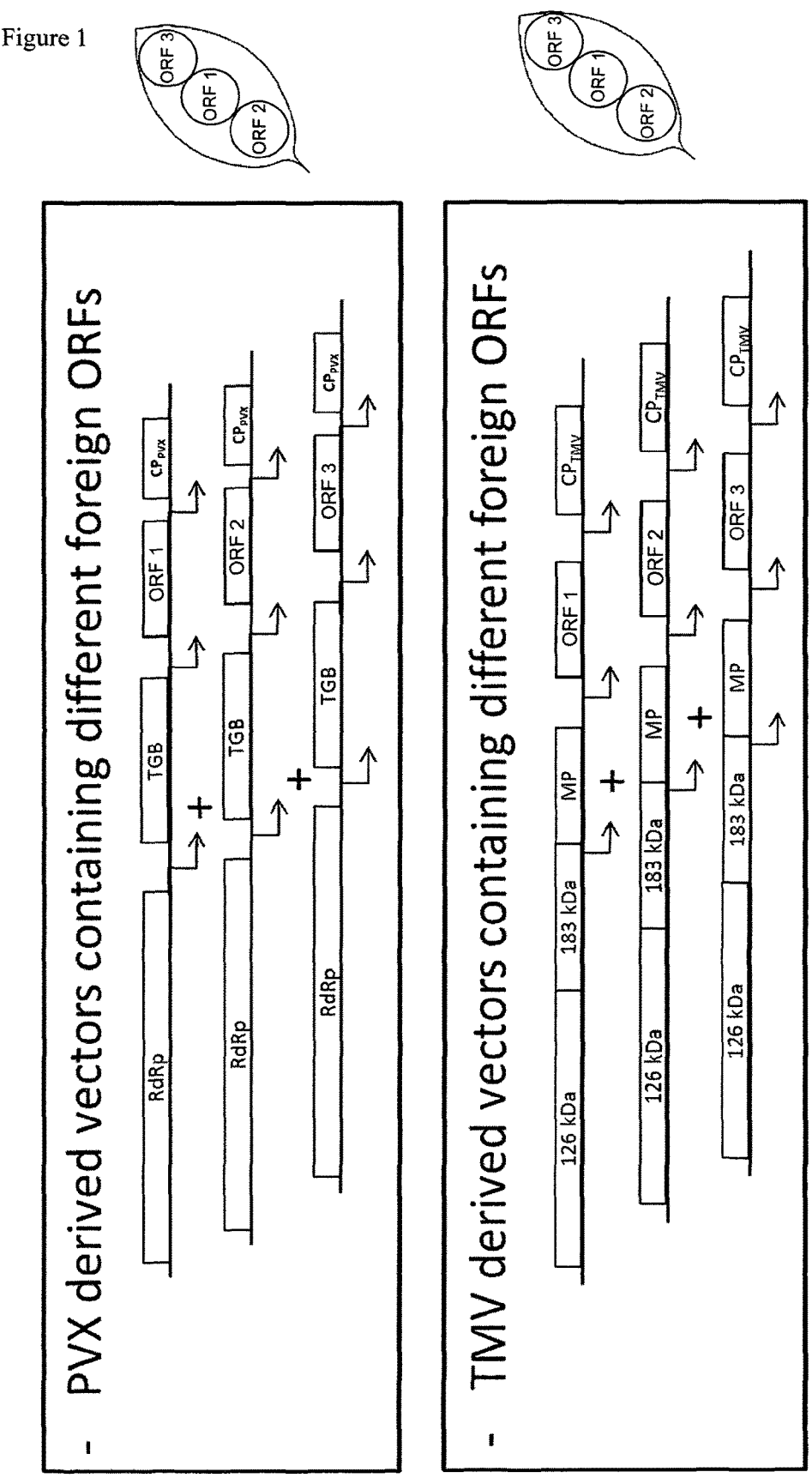

For the recombinant production of proteins in plants, the use of viral vectors represents a promising alternative to the production of transgenic plants. Viral vectors allow high yields of proteins of interest, as their genomes are present in high concentrations in plant cells due to efficient replication. Moreover, it is possible to wait with infection and subsequent production until a certain developmental stage of the host plant is accomplished and also a higher biomass becomes available. However, the production of different recombinant proteins in the same cell represents a problem when using different viral vectors derived from the same genome. This is in particular a problem when complex proteins comprising more than one polypeptide chains should be produced. When two vectors derived from one viral species with coding sequences for two different foreign proteins are co-inoculated in one plant, the two viral vectors segregate spatially in the course of infection. This dilemma is shown in FIG. 1. Only in the area of the originally infected cells, a few cells can be found in which both vectors can be detected. In the systemically infected plants, either only one of vectors will be present, or areas can be found in which either only the one or the other vector is present. Therefore, the expression of different proteins in the same plant cell by means of viral vectors is still a challenge. Moreover, a lot of plant viruses are transmitted mechanically or with the aid of insects. Therefore, whole viral genomes with the capability to infect plants systemically may be liberated into the environment.

Existing approaches to overcome the problems employ non-competitive viral vectors as the Tobacco Mosaic Virus (TMV), and the Potato Virus X (PVX), aiming at very rapid and high production (US 2009/0111145 A1; EP 1 686 176 A1) (see FIG. 2). However, in order to produce more complex proteins, further non-competitive viral vectors would be necessary, which would represent an additional burden for the infected plant.

Therefore, it was the object of the present invention to make available kits and methods which allow recombinant production of two or more polypeptides simultaneously in plant cells, and which at the same time ensures a biosafety containment.

In one embodiment, the object is solved by a kit comprising
 a) a first plus-sense single stranded RNA viral vector, and
 b) a second plus-sense single stranded RNA viral vector, wherein
 (i) the first plus-sense single-stranded viral vector and the second plus-sense single-stranded viral vector are derived from different plant viruses, and
 (ii) the coat protein ORF of the virus from which the first vector is derived is completely deleted in the first plus-sense single stranded RNA viral vector, and
 (iii) the coat protein ORF of the virus from which the second vector is derived is completely deleted in the second plus-sense single stranded RNA viral vector, and
 (iv) the first plus-sense single stranded RNA viral vector comprises a functional coat protein ORF of the virus from which the second plus-sense single-stranded viral vector is derived, and
 (v) the second plus-sense single stranded RNA viral vector comprises a functional coat protein ORF of the virus from which the first plus-sense single-stranded viral vector is derived, and
 (vi) the first plus-sense single-stranded viral vector and the second plus-sense single-stranded viral vector comprise an RNA replicon which is able to replicate in plant cells.

Surprisingly it was found that a kit comprising such a first and second vector enables systemic co-infection of single cells, and both gene products are present, as shown in Example 1.

Due to the complete deletion of the coat protein ORF and the insertion of the coat protein ORF of the respective other virus, a kit is prepared which allows for systemic co-infection and co-expression. At the same time, a containment system is obtained, as the systemic infection of a healthy plant after liberation of a single vector into the environment is not possible. Due to the combined systemic infection, the complexity regarding the devices needed for infection is much lower, as not all plant parts need to be infected individually. Preferably, the coat proteins are reciprocally exchanged; i.e. the coat protein ORF of the virus from which the first plus-sense single-stranded viral vector is derived is replaced by the functional coat protein ORF of the virus from which the second plus-sense single-stranded viral vector is derived, and vice versa. Such replacement is preferred, as this does not disturb the overall viral genome organization and does not generate excessive additional genome load.

Thus, in a preferred embodiment of the kit, the coat protein ORF of the virus from which the first plus-sense single-stranded viral vector is derived is replaced by the functional coat protein ORF of the virus from which the second plus-sense single-stranded viral vector is derived.

In a further preferred embodiment, the coat protein ORF of the virus from which the second plus-sense single-stranded viral vector is derived is replaced by the functional coat protein ORF of the virus from which the first plus-sense single-stranded viral vector is derived.

As explained above, the kits of the invention represent non-competitive viral vectors. Therefore, in a yet further preferred embodiment, the viruses from which the first and second plus-sense single-stranded viral vectors are derived belong to different virus types, preferably different virus genera, more preferably to different virus families.

It is particularly preferred to make use of the non-competitive TMV- and PVX-viruses. Such kit based on TMV- and PVX-viruses was successfully used in Example 1.

The TMV genome encodes at least four proteins: the 126 and 183-kDa replicase proteins, the 30-kDa cell-to-cell movement protein (MP), and the 17.5-kDa coat protein (CP). The MP and the CP are encoded by subgenomic RNAs, which are co-terminal with the 3' end of genomic RNA (see FIG. 2).

The PVX genome encodes at least five proteins: the RNA-dependent RNA-polymerase (RdRp), the triple gene block proteins 1-3 (TGBp25, TGBp12, TGBp8) and the 25 kDa coat protein (CP). The TGB proteins and the CP are encoded by subgenomic RNAs, which are co-terminal with the 3' end of the genomic RNA (see FIG. 2).

Potexviruses and Tobamoviruses are plant RNA viruses with a plus-sense single-stranded genome. Their genome is monopartite.

Thus, said viral vectors of the invention may be RNA being or comprising said RNA replicon or may be DNA encoding said RNA replicon.

A RNA replicon comprises the elements of viral vectors of kits of the invention. Further genetic elements will typically be present on said replicon for replication and expression. For being a RNA replicon, i.e. for autonomous replication in a plant cell, said RNA replicon encodes a RdRp or a functional derivative thereof.

Said RNA replicon preferably further has viral, in particular tobamoviral or potexviral 5'- or 3'-untranslated regions and promoter-sequences in the 5'- or 3'-untranslated regions of said RNA replicon for binding said RdRp and for replicating said RNA replicon.

Said RNA replicon further may have subgenomic promoters for generating subgenomic RNAs for the expression of the CP (coat protein), MP (movement protein(s)) or TGB (triple gene block proteins) or functional heterologous ORF proteins, where applicable.

If said viral vector is DNA, it will typically have a promoter for allowing infectious RNA production by transcription of said RNA replicon in vitro or in vivo in plants. An example of a promoter allowing for transcription of said RNA replicon from DNA in plants is the 35S promoter of Cauliflower mosaic virus that is widely used in plant biotechnology.

The RdRp used in viral vectors may be considered a functional variant of a viral RdRp if the sequence encodes a protein having a sequence identity of at least 50%, preferably at least 60%, more preferably at least 80%, and most preferably at least 90% of the native RdRp.

A list of plus-sense single stranded RNA viruses that can be used for engineering the viral vectors of the invention is presented below:
Family: Bromoviridae,
Genus: Alfamovirus, Type species: alfalfa mosaic virus,
Genus: Ilarvirus, Type species: tobacco streak virus,
Genus: Bromovirus, Type species: brome mosaic virus,
Genus: Cucumovirus, Type species: cucumber mosaic virus;
Family: Closteroviridae,
Genus: Closterovirus, Type species: beet yellows virus,
Genus: Crinivirus, Type species: Lettuce infectious yellows virus,
Family: Comoviridae,
Genus: Comovirus, Type species: cowpea mosaic virus,
Genus: Fabavirus, Type species: broad bean wilt virus 1,
Genus: Nepovirus, Type species: tobacco ringspot virus;
Family: Potyviridae,
Genus: Potyvirus, Type species: potato virus Y, plum pox virus; tobacco etch virus; clover yellow vein virus; tobacco vein mottling virus;
Genus: Rymovirus, Type species: ryegrass mosaic virus,
Genus: Bymovirus, Type species: barley yellow mosaic virus;
Family: Sequiviridae,
Genus: Sequivirus, Type species: parsnip yellow fleck virus,
Genus: Waikavirus, Type species: rice tungro spherical virus;
Family: Tombusviridae,
Genus: Carmovirus, Type species: carnation mottle virus,
Genus: Dianthovirus, Type species: carnation ringspot virus,
Genus: Machlomovirus, Type species: maize chlorotic mottle virus,
Genus: Necrovirus, Type species: tobacco necrosis virus,
Genus: Tombusvirus, Type species: tomato bushy stunt virus,
Unassigned Genera of ssRNA Viruses:
Genus: Capillovirus, Type species: apple stem grooving virus;
Genus: Carlavirus, Type species: carnation latent virus;
Genus: Enamovirus, Type species: pea enation mosaic virus,
Genus: Furovirus, Type species: soil-borne wheat mosaic virus,
Genus: Hordeivirus, Type species: barley stripe mosaic virus,
Genus: Idaeovirus, Type species: raspberry bushy dwarf virus;
Genus: Luteovirus, Type species: barley yellow dwarf virus;
Genus: Marafivirus, Type species: maize rayado fino virus;
Genus: Potexvirus, Type species: potato virus X;
Genus: Sobemovirus, Type species: Southern bean mosaic virus,
Genus: Tenuivirus, Type species: rice stripe virus,
Genus: Tobamovirus, Type species: tobacco mosaic virus,
Genus: Tobravirus, Type species: tobacco rattle virus,
Genus: Trichovirus, Type species: apple chlorotic leaf spot virus;
Genus: Tymovirus, Type species: turnip yellow mosaic virus;
Genus: Umbravirus, Type species: carrot mottle virus;

Thus, in a yet further preferred embodiment, the virus from which the first plus-sense single-stranded viral vector is derived is a Potexvirus, in particular PVX virus (potato virus X).

In a yet further preferred embodiment, the virus from which the second plus-sense single-stranded viral vector is derived is a Tobamovirus, in particular TMV virus (tobacco mosaic virus).

In Example 1, the first and second plus-sense single-stranded viral vectors comprise a heterologous ORF. Thus, it is possible to produce two different heterologous proteins in a plant cell using such first and second plus-sense single-stranded viral vectors (see FIG. 3). Preferred vectors, as used in Example 1, have the structure PVX-CP(TMV)-ORF and TMV-CP(PVX)-ORF.

Figure 3:
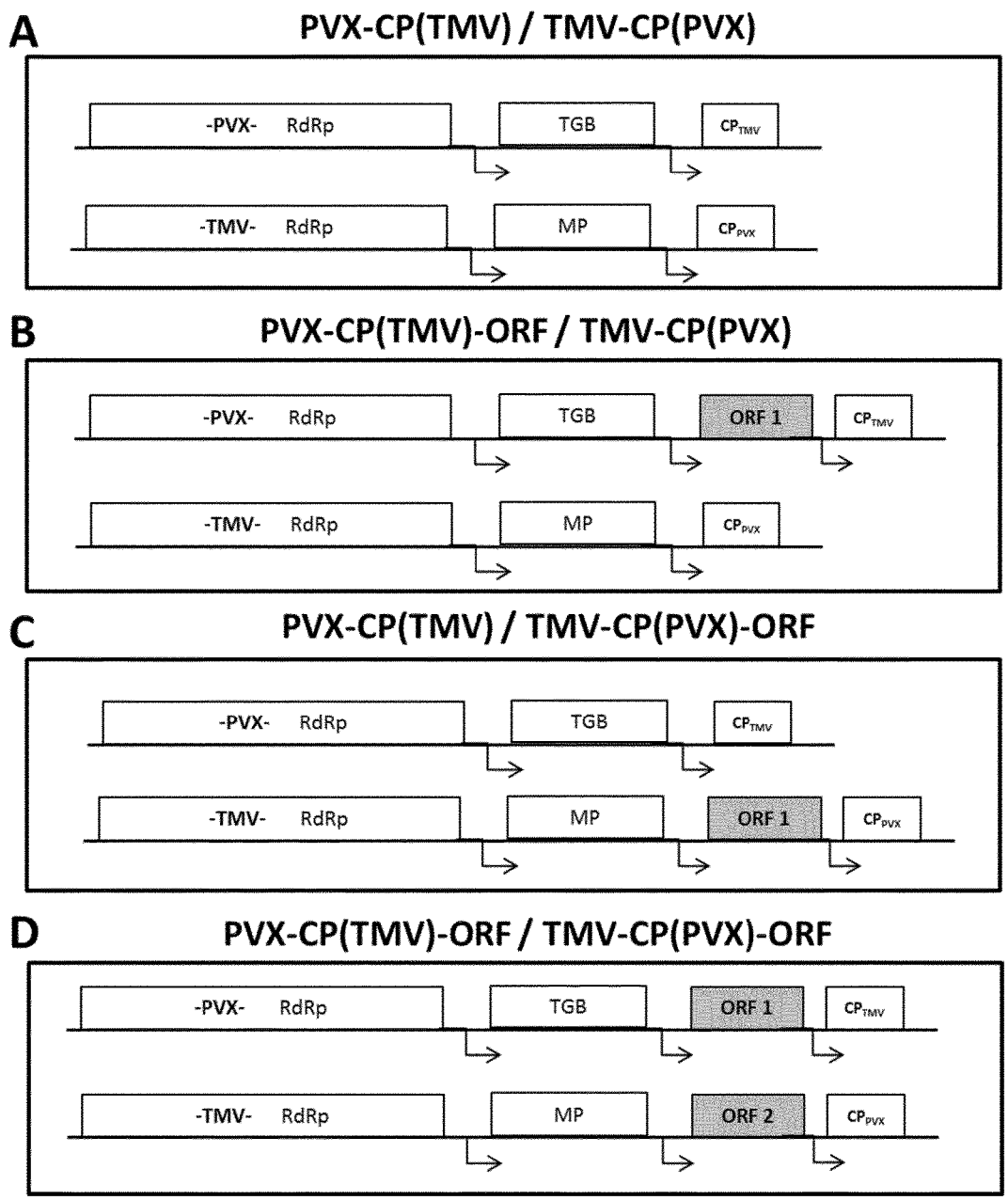

However, it is not required, that these vectors comprise such heterologous ORFs. Rather, the plus-sense single-stranded viral vectors may be used in one preferred embodiment only as complementing vectors. In such embodiment either of the vectors or both do not comprise a heterologous ORF. Preferred viral vector combinations are vector combinations having the following structures: (a) PVX-CP(TMV) and TMV-CP(PVX); (b) PVX-CP(TMV)-ORF and TMV-CP(PVX); (c) PVX-CP(TMV) and TMV-CP(PVX)-ORF and PVX-CP(TMV)-ORF and TMV-CP(PVX)-ORF (as shown in FIG. 3).

Thus in another preferred embodiment of the invention, the first plus-sense single-stranded viral vector and/or the second plus-sense single-stranded viral vector comprise a functional heterologous ORF. The ORF may be the same or different, preferably different. In such embodiment, the vectors are used as complementing vectors and in addition are used for expressing a heterologous ORF of interest.

For being expressible from the viral vectors in a plant or in plant tissue, said viral vectors comprising a functional heterologous ORF comprise one or more subgenomic promoters and other sequences required for expression such as ribosome binding site and/or an internal ribosome entry site (IRES).

Thus in another preferred embodiment of the invention, the first plus-sense single-stranded viral vector and/or the second plus-sense single-stranded viral vector do not comprise a functional heterologous ORF. In this embodiment, the kit is used as complementing viral vector kit, which can be used to add further viral vector(s) comprising functional heterologous ORF(s), as described below which do not comprise a coat protein.

It was surprisingly found that using the complementing vector pair PVX-CP(TMV)-ORF and TMV-CP(PVX)-ORF, and the coat-protein-deficient vector PVX-ΔCP-ORF, it is possible to achieve expression of all ORFs, as described in Example 1. Therefore, it was surprisingly found that further heterologous ORFs may be expressed in the same plant cells based on the complementing vectors and one or more further vectors carrying heterologous ORF(s), wherein the further vectors have a complete deletion of the coat protein. Due to the complete deletion, the genomic load of virus is considerably lower and the coat protein deficiency of the further vectors comprise additional containment (FIGS. 3 and 4).

"PVX-CP(TMV)-ORF" is understood as viral vector based on PVX, wherein the native coat protein is replaced by the coat protein of TMV, and wherein the vector comprises a functional heterologous ORF.

"TMV-CP(PVX)-ORF" is understood as viral vector based on TMV, wherein the native coat protein is replaced by the coat protein of PVX, and wherein the vector comprises a functional heterologous ORF.

"PVX-ΔCP-ORF" is understood as viral vector based on PVX, wherein the native coat protein ORF is completely deleted, and wherein the vector comprises a functional heterologous ORF (see also FIG. 4).

"PVX-ΔCP-ΔMPs-ORF" is understood as viral vector based on PVX, wherein the native coat protein ORF is completely deleted, and wherein the viral vector is devoid of functional movement proteins, and wherein the vector comprises a functional heterologous ORF (see also FIG. 5). In a preferred embodiment, the movement proteins are completely deleted.

"PVX-ORF" is understood as viral vector based on PVX, wherein the vector comprises a functional heterologous ORF.

"TMV-ORF" is understood as viral vector based on TMV, wherein the vector comprises a functional heterologous ORF.

A "functional heterologous ORF" is understood as open reading frame (ORF), which is not present in the respective unmodified virus, and which can be expressed to yield a functional gene product. Such gene product may be RNA or a protein, preferably a protein. Preferably, the functional heterologous ORF is heterologous for all viral vectors used. Typically, the functional heterologous ORF is under control of suitable subgenomic promoters or ribosome-binding sites or IRES.

Therefore, in one particularly preferred embodiment, this further viral vector is a third plus-sense single stranded RNA viral vector with the following features:

In a particularly preferred embodiment, the kit further comprises
a) at least one third plus-sense single stranded RNA viral vector,
  wherein
  (i) the at least one third plus-sense single-stranded viral vector(s) comprise(s) at least one functional heterologous ORF, and
  (ii) the at least one third plus-sense single-stranded viral vector(s) is/are derived from the same plant virus as the first or second plus-sense single-stranded viral vector, and
  (iii) the coat protein ORF of the virus from which the at least one third plus-sense single-stranded viral vector(s) are derived is completely deleted in the at least one third plus-sense single stranded RNA viral vector(s) and/or
b) at least one additional plus-sense single stranded RNA viral vector,
  wherein
  (i) the at least one additional plus-sense single-stranded viral vector(s) comprise(s) at least one functional heterologous ORF, and
  (ii) the at least one additional plus-sense single-stranded viral vector(s) is/are derived from the same plant virus as the first or second plus-sense single-stranded viral vector.

Moreover, it is possible to additionally delete the movement protein(s) of the third plus-sense single-stranded viral vector(s), thereby further reducing viral genomic size.

Thus, in a particularly preferred embodiment, the at least one third plus-sense single stranded RNA viral vector(s) is/are devoid of the functional movement protein ORF(s) of the virus from which the at least one third plus-sense single-stranded viral vector(s) are derived, preferably the functional movement protein ORF(s) of the virus from which the at least one third plus-sense single-stranded viral vector(s) are derived are completely deleted (see also FIG. 4).

Thus in a preferred embodiment, the virus from which the third plus-sense single-stranded viral vector is derived is a Potexvirus, in particular PVX virus (potato virus X) and the third plus-sense single-stranded viral vector is devoid of the functional movement protein ORF(s) of the Potexvirus.

As shown in the Example 1, the complementation was achieved using PVX-ΔCP-ORF as third viral vector. Such a vector is a preferred vector for a kit according to the invention.

In a further embodiment, the movement proteins of PVX may be deleted. Such vector has the structure PVX-ΔCP-ΔTGB-ORF.

The generation of such deletion is described in Example 1.

Thus, in a particularly preferred embodiment, the virus from which the third plus-sense single-stranded viral vector is derived is a Potexvirus, in particular PVX virus (potato virus X). Even more preferred are vectors of the structure PVX-ΔCP-ΔTGB-ORF and/or PVX-ΔCP-ORF.

Therefore, in a particularly preferred embodiment of the invention, the virus from which the first plus-sense single-stranded viral vector is derived is a Potexvirus, in particular PVX virus (potato virus X), and the virus from which the second plus-sense single-stranded viral vector is derived is a Tobamovirus, in particular TMV virus (tobacco mosaic virus), and the third plus-sense single-stranded viral vector is derived is a Potexvirus, in particular PVX virus (potato virus X).

In an even more preferred embodiment, the kit comprises or contains
(A)
  (i) vectors of the structure PVX-CP(TMV) and TMV-CP (PVX); or
  (ii) vectors of the structure PVX-CP(TMV)-ORF and TMV-CP(PVX); or (iii) vectors of the structure PVX-CP(TMV) and TMV-CP(PVX)-ORF or (iv) vectors of the structure PVX-CP(TMV)-ORF and TMV-CP(PVX-ORF) and (B) a vector of the structure PVX-ΔCP-ΔTGB-ORF or PVX-ΔCP-ORF.

In Example 1, also the complementing vectors comprise a heterologous ORF. It is however also possible that only the at least one third plus-sense single-stranded viral vector(s) comprise a heterologous ORF in order to reduce viral vector size of the complementing vectors. Also, it is preferred that one viral vector comprises only one heterologous ORF, in order to reduce excessive viral genomic size.

In yet another preferred embodiment, the at least one additional plus-sense single stranded RNA viral vector(s) comprises the features of a first or second plus-sense single-stranded viral vector described above, and comprises at least one functional heterologous ORF, wherein the at least one functional heterologous ORF is different from the functional heterologous ORF(s) of the first or second plus-sense single-stranded viral vector, in case one or both of the vectors comprise functional heterologous ORF(s).

Such additional plus-sense single stranded RNA viral vector(s) is obtainable by replacing (in case a functional heterologous ORF is present) or introducing (in case no functional heterologous ORF is present) a functional heterologous ORF in the first or second plus-sense single stranded RNA viral vector.

Thus, in a preferred embodiment preferably the at least one additional plus-sense single stranded RNA viral vector(s) differs from the first or second plus-sense single-stranded viral vector by a functional heterologous ORF.

In a yet further preferred embodiment, the at least one additional plus-sense single stranded RNA viral vector(s) is/are derived from the same virus from which the first plus-sense single-stranded viral vector or the second plus-sense single-stranded viral vector is derived, and comprises at least one functional heterologous ORF. In particularly preferred embodiment, a wt viral vector may be used to introduce at least one functional heterologous ORF in order to obtain such additional plus-sense single stranded RNA viral vector. In another particularly preferred embodiment, the at least one additional plus-sense single stranded RNA viral vector(s) comprises the coat protein, the movement protein(s) and RNA-dependent RNA polymerase of the virus from which the first plus-sense single-stranded viral vector or the second plus-sense single-stranded viral vector is derived, and at least one functional heterologous ORF. Such at least one functional heterologous ORF may be the same or different functional heterologous ORF as in the first plus-sense single-stranded viral vector or the second plus-sense single-stranded viral vector (in case they comprise such functional heterologous ORF), preferably different.

Thus, preferably, two or more different third and/or additional plus-sense single stranded RNA viral vectors comprise different functional heterologous ORF(s).

In a further preferred embodiment, at least one third and/or additional plus-sense single stranded RNA viral vector(s) comprise one functional heterologous ORF.

Said viral vectors may be built on a natural plus-sense single-stranded virus e.g. by using genetic components from such a virus, in particular Tobamovirus or Potexvirus. Said viral vectors of the invention or of kits of the invention may be obtainable by inserting said heterologous ORF sequences into viral vectors encoding a virus and by replacing the sequence encoding a CP as described above. However, various modifications may be made to the various genetic components of a natural virus, such as to the RdRp gene of the Potexvirus, or to the 5' or 3' non-translated regions of a Potexvirus.

The viral vectors of the kits of the invention may be mixed, to obtain mixtures of such viral vectors. Such mixtures are e.g. in solid form, such as a dried or freeze-dried solid, or in a liquid, e.g. as aqueous solution, suspension or dispersion, or as gels. Such mixtures can be used to infect plants, plant cells or plant tissues.

Therefore, the present invention also relates to a mixture comprising 2, 3, or more different vectors of the following vectors a) to c):

a) at least one first plus-sense single stranded RNA viral vector as defined above, b) at least one second plus-sense single stranded RNA viral vector as defined above, c) at least one additional and/or third plus-sense single stranded RNA viral vector as defined above.

In Example 1, a mixture of or PVX-ΔCP-ORF, PVX-CP (TMV)-ORF and TMV-CP(PVX)-ORF was used successfully for infection.

In a preferred embodiment, the mixture comprises (i) at least one first plus-sense single stranded RNA viral vector as defined above, and (ii) at least one second plus-sense single stranded RNA viral vector as defined above, and (iii) optionally at least one third and/or additional plus-sense single stranded RNA viral vector as defined above.

In a further preferred embodiment, the mixture comprises (i) at least one third and/or additional plus-sense single stranded RNA viral vector as defined above, and (ii) at least one first plus-sense single stranded RNA viral vector as defined above, and/or at least one second plus-sense single stranded RNA viral vector as defined above.

The kits and mixtures of the invention may be used for successfully infecting plants or plant cells with the vectors as described above.

Thus the present invention also relates to a plant or plant cell comprising at least one first plus-sense single stranded RNA viral vector and at least one second plus-sense single stranded RNA viral vector as defined above, and optionally at least one third and/or additional plus-sense single stranded RNA viral vector(s) as defined above.

For the first time, it is now possible to obtain simultaneous co-expression of the different heterologous ORFs of the vectors systemically in more than one plant cell in more than one tissue using plant RNA viral vectors.

Therefore, preferably more than one plant cell in more than one tissue comprises at least one first plus-sense single stranded RNA viral vector and at least one second plus-sense single stranded RNA vector, and optionally at least one third and/or additional plus-sense single stranded RNA viral vector(s), as described above.

Therefore, in another preferred embodiment, more than one plant cell in more than one tissue comprises the heterologous polypeptides encoded by the ORFs of at least two different third and/or additional plus-sense single stranded RNA viral vector(s) as defined herein.

The kits and mixtures of the invention can be used for expression of heterologous proteins. In particular, the kits allow for the first time the contained production of heterooligomeric proteins in systemically infected plants using viral vectors for commercial applications.

Therefore, the invention relates in one embodiment to a method for producing in a plant, or plant tissue, or plant cell a heterooligomeric polypeptide and/or two or more polypeptides, comprising providing to at least one plant cell
  (i) at least one first plus-sense single stranded RNA viral vector, as defined herein, and
  (ii) at least one second plus-sense single stranded RNA viral vector, as defined herein, and
  (iii) optionally at least one third and/or additional plus-sense single stranded RNA viral vector, as defined herein,
  wherein
  a) at least two third and/or additional plus-sense single stranded RNA viral vectors are provided to at least one plant cell if the first plus-sense single stranded RNA viral vector and the second plus-sense single stranded RNA viral vector do not comprise a functional heterologous ORF, and
  b) wherein at least two of the viral vectors according to (i) to (iii) comprise different heterologous ORFs.

In a particularly preferred embodiment, the method is followed by isolating the heterooligomeric polypeptide and/or two or more polypeptides from the plant, plant tissue, or plant cell.

Methods for isolating proteins from plants or plant cells are known in the art. In one method, a protein of interest may be isolated from a plant apoplast as described in WO 03/020938.

Surprisingly, systemic infection with all vectors can be achieved using the vectors of the kits. Therefore, in a preferred embodiment, systemic infection of the plant is achieved.

The method is in particular useful for producing heterooligomeric proteins, which should be produced in one cell and should be assembled in such cell to yield a functional protein. Examples of such heterooligomeric proteins are immunoglobulins, in particular an antibody or antibody fragment, or certain interleukins, such as IL-12.

*Agrobacterium*-mediated delivery of viral vectors in plant cells may be used for the provision of viral vectors. Various other methods usually used for stable transformation of plants may also be used for the provision of viral vectors into plant cells such as direct introduction of a nucleic acid sequence into cells by means of microprojectile bombardment, electroporation or PEG-mediated transformation of protoplasts. *Agrobacterium*-mediated plant transformation is preferred. Thus, a heterologous nucleotide sequence may be transformed into plant cells by various technologies such as by a Ti-plasmid vector carried by *Agrobacterium* (U.S. Pat. Nos. 5,591,616; 4,940,838; 5,464,763), particle or microprojectile bombardment (U.S. Pat. No. 5,100,792; EP00444882 B1; EP 00434616 B1). In principle, other plant transformation methods can also be used e.g. microinjection (WO 09/209696; WO 09/400583A1; EP 175966 B1), electroporation (EP00564595 B1; EP00290395 B1; WO 08/706614 A1), etc. The choice of the transformation method depends inter alia on the plant species to be transformed. For example, microprojectile bombardment may be preferred for monocot transformation, while for dicots, *Agrobacterium*-mediated transformation gives generally better results.

The present invention is preferably carried out with higher, multi-cellular plants. Preferred plants for the use in this invention include any plant species with preference given to agronomically and horticulturally important species. Common crop plants for the use in present invention include alfalfa, barley, beans, canola, cowpeas, cotton, corn, clover, lotus, lentils, lupine, millet, oats, peas, peanuts, rice, rye, sweet clover, sunflower, sweetpea, soybean, sorghum triticale, yam beans, velvet beans, vetch, wheat, wisteria, and nut plants. The plant species preferred for practicing of this invention are including but not restricted to: Representatives of *Graminae*, *Compositae*, *Solanacea* and *Rosaceae*. Additionally, preferred species for use in the invention, as well as those specified above, plants from the genera: *Arabidopsis, Agrostis, Allium, Antirrhinum, Apium, Arachis, Asparagus, Atropa, Avena, Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum, Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza, Panicum, Pelargonium, Pennisetum, Petunia, Pisum, Phaseolus, Phleum, Poa, Prunus, Ranunculus, Raphanus, Ribes, Ricinus, Rubus, Saccharum, Salpiglossis, Secale, Senecio, Setaria, Sinapis, Solanum, Sorghum, Stenotaphrum, Theobroma, Trifolium, Trigonella, Triticum, Vicia, Vigna, Vitis, Zea*, and the *Olyreae*, the *Pharoideae* and many others.

Preferred plants are *Nicotiana* species like *Nicotiana benthamiana* and *Nicotiana tabacum*; preferred plant species other than *Nicotiana* species are *Petunia hybrida, Brassica campestris, B. juncea*, cress, arugula, mustard, Strawberry, spinach, *Chenopodium capitatum*, alfalfa, lettuce, sunflower, potato and cucumber.

Preferred Potexviruses are PVX, bamboo mosaic virus, papaya mosaic virus, alternanthera mosaic virus, clover yellow mosaic virus, plantain virus X, white clover mosaic virus and potato aucuba mosaic virus, in particular potato virus X (PVX).

The major application of the present invention is the production of a protein of interest in plants, plant leaves or plant tissue or cell culture. If the process of the invention is performed in plants, plants that do not enter the human or animal food chain are preferred, like *Nicotiana* species. Plants that do not enter the human or animal food chain can be cultivated in an open field and harvested within certain period after infection with said viral vectors. Preferably, whole plants or plant parts shall be confined to a contained environment, e.g. a glasshouse or a designed chamber for the incubation period necessary to provide for desired level of expression.

In a further embodiment, the present invention relates to a PVX virus vector, wherein
  a) the functional coat polypeptide ORF of the PVX virus is completely deleted, and
  b) the PVX viral vector comprises an RNA replicon which is able to replicate in plant cells, and
  c) the PVX virus vector optionally comprises at least one functional heterologous ORF, and
  d) the PVX virus vector optionally comprises a functional coat polypeptide ORF of a different virus.

It was surprisingly found that complete deletion of the PVX coat protein allows successful co-infection. In the state of the art, deletions of the coat protein resulted in vectors wherein the 3' end of the coat protein was still present. Such vectors are described in Komarova et al. (2006, Biochemistry (Mosc); 71: 846-850) and Tyulkina et al. (2011, Acta naturae; 3: 73-82). However, such partial deletion of the ORF is insufficient for achieving coinfection. Therefore, the novel PVX vectors of the invention are surprisingly useful for coinfection, in particular with the complementing vectors of the kits of the invention above.

In another embodiment of the invention, it is also possible to make use of coat-protein deficient viral vectors for infection of plants without the danger of a contamination of the environment. In this embodiment, at least two viral vectors with the same backbone are used, which lack their native coat protein. Due to the coat protein deficiency, a systemic infection and/or contamination of the environment are not possible. Using the same backbone for expression of two or more different heterologous ORFs allows simple construction of the vectors. Moreover, the deletion of coat protein allows introduction of a heterologous ORF without excessive increase of viral genome size. Moreover, as the vectors can replicate within the plant cells, higher protein expression yields can be achieved compared to a simple transient expression using *A. tumefaciens* cells (Example 2).

Therefore, in another embodiment, the present invention relates to a method for producing in a plant, or plant tissue, or plant cell a heterooligomeric polypeptide and/or two or more polypeptides, comprising providing to a plant, or plant tissue, or plant cell at least two plus-sense single stranded RNA viral vectors,
  a) wherein the at least two plus-sense single stranded RNA viral vectors are derived from the same virus, and
  b) wherein at least two plus-sense single stranded RNA viral vectors comprise different functional heterologous ORFs, and
  c) wherein the at least two plus-sense single stranded RNA viral vectors are devoid of the functional coat protein ORF of the virus from which the vectors are derived, and
  d) wherein the at least two plus-sense single stranded RNA viral vectors comprise an RNA replicon which is able to replicate in plant cells.

In a particularly preferred embodiment, the coat proteins are completely deleted. Therefore, in a preferred embodiment, the coat protein ORF of the virus from which the at least two plus-sense single stranded RNA viral vectors are derived, is completely deleted in the at least two plus-sense single stranded RNA viral vectors.

In a further preferred embodiment, the virus from which the at least two plus-sense single stranded RNA viral vectors are derived is a Potexvirus, in particular PVX virus (potato virus X).

In an even more preferred embodiment, the coat protein ORF of the virus from which the at least two plus-sense single stranded RNA viral vectors are derived, is completely deleted in the at least two plus-sense single stranded RNA viral vectors, and the virus from which the at least two plus-sense single stranded RNA viral vectors are derived is a Potexvirus, in particular PVX virus (potato virus X).

A variety of methods are known to provide the vectors to the plant, or plant tissue, or plant cell. In particular, they may be provided by agroinfection, by transfection with DNA, in particular DNA comprising cDNA of the viral genome, by transfection with RNA, in particular RNA corresponding to the virus genome. Such methods are for example described in Fischer, R., et al. (2004; Plant-based production of biopharmaceuticals. Curr Opin Plant Biol 7, 152-158); Komarova, T. V. et al. (2010; Transient expression systems for plant-derived biopharmaceuticals. Expert Rev Vaccines 9, 859-876) and Lico, C. et al. (2012; The use of plants for the production of therapeutic human peptides. Plant Cell Rep 31, 439-451).

Alternatively, the cloned cDNAs of the viral genomes may be used for transcribing the RNA in vitro, which is then used for infection.

Alternatively, the cloned cDNAs of the viral genomes may be cloned into suitable vector constructs, such as plasmids or DNA fragment, which allow transcription of the genome. In particular, such construct comprises suitable promoter and terminator sequences.

In case of agroinfection, the cDNA of the viral genome is introduced into T-DNA, which is then provided to the plants. Again such T-DNA comprises further regulatory DNA components, which allow transcription of the genome. In particular, such T-DNA construct comprises suitable promoter and terminator sequences.

The different *Agrobacterium* cell cultures, which comprise the respective viral vectors comprising the different functional heterologous ORFs may be mixed and may be administered to plants for infection.

Therefore, in one embodiment, the present invention relates to a mixture of *Agrobacterium* cells, in particular *Agrobacterium tumefaciens* cells,
  a) wherein a plurality of *Agrobacterium* cells comprise at least one plus-sense single stranded RNA viral vector comprising at least one functional heterologous ORF,
    i) wherein the at least one plus-sense single stranded RNA viral vector is devoid of the functional coat protein ORF, and
    ii) wherein the at least one plus-sense single stranded RNA viral vector comprises an RNA replicon which is able to replicate in plant cells,
  and
  b) wherein at least two *Agrobacterium* cells comprise different plus-sense single stranded RNA vectors comprising different functional heterologous ORFs, and
  c) wherein the different plus-sense single stranded RNA vectors comprise different functional heterologous ORFs are derived from the same virus.

In a preferred embodiment of the present invention, at least two, three, four, five or more *Agrobacterium* cells comprise two, three, four, five or more two, three, four, five or more, even more preferably two *Agrobacterium* cells in the mixture comprise different plus-sense single stranded RNA vectors. Even more preferably, the two *Agrobacterium* cells in the mixture each contain one plus-sense single stranded RNA vector.

In a further preferred embodiment, the virus from which the plus-sense single stranded RNA viral vectors are derived is a Potexvirus, in particular PVX virus (potato virus X).

In a further preferred embodiment, the coat protein ORF of the virus from which the plus-sense single stranded RNA viral vectors are derived, is completely deleted in the plus-sense single stranded RNA viral vectors.

In a yet further preferred embodiment of the invention, the virus from which the plus-sense single stranded RNA viral vectors are derived is a Potexvirus, in particular PVX virus (potato virus X) and the coat protein ORF of the virus from which the plus-sense single stranded RNA viral vectors are derived, is completely deleted in the plus-sense single stranded RNA viral vectors.

Proteins of interest, or fragments thereof, that can be expressed, in sense or antisense orientation, using the invention include: starch modifying enzymes (starch synthase, starch phosphorylation enzyme, debranching enzyme, starch branching enzyme, starch branching enzyme II, granule bound starch synthase), sucrose phosphate synthase, sucrose phosphorylase, polygalacturonase, polyfructan sucrase, ADP glucose pyrophosphorylase, cyclodextrin glycosyl-transferase, fructosyl transferase, glycogen synthase, pectin esterase, aprotinin, avidin, bacterial levansucrase, *E. coli* glgA protein, MAPK4 and orthologues, nitrogen assimilation/methabolism enzyme, glutamine synthase, plant osmotin, 2S albumin, thaumatin, site-specific recombinase/integrase (FLP, Cre, R recombinase, Int, SSVI Integrase R, Integrase phiC31, or an active fragment or variant thereof), isopentenyl transferase, Sca M5 (soybean calmodulin), coleopteran type toxin or an insecticidally active fragment, ubiquitin conjugating enzyme (E2) fusion proteins, enzymes that metabolize lipids, amino acids, sugars, nucleic acids and polysaccharides, superoxide dismutase, inactive proenzyme form of a protease, plant protein toxins, traits altering fiber in fiber producing plants, Coleopteran active toxin from *Bacillus thuringiensis* (Bt2 toxin, insecticidal crystal protein (ICP), CrylC toxin, delta endotoxin, polyopeptide toxin, protoxin etc.), insect specific toxin AaIT, cellulose degrading enzymes, E1 cellulase from Acidothermus celluloticus, lignin modifying enzymes, cinnamoyl alcohol dehydrogenase, trehalose-6-phosphate synthase, enzymes of cytokinin metabolic pathway, HMG-CoA reductase, *E. coli* inorganic pyrophosphatase, seed storage protein, *Erwinia* herbicola lycopen synthase, ACC oxidase, pTOM36 encoded protein, phytase, ketohydrolase, acetoacetyl CoA reductase, PHB (polyhydroxybutanoate) synthase, acyl carrier protein, napin, EA9, non-higher plant phytoene synthase, pTOM5 encoded protein, ETR (ethylene receptor), plastidic pyruvate phosphate dikinase, nematode-inducible transmembrane pore protein, trait enhancing photosynthetic or plastid function of the plant cell, stilbene synthase, an enzyme capable of hydroxylating phenols, catechol dioxygenase, catechol 2,3-dioxygenase, chloromuconate cycloisomerase, anthranilate synthase, *Brassica* AGL15 protein, fructose 1,6-biphosphatase (FBPase), AMV RNA3, PVY replicase, PLRV replicase, potyvirus coat protein, CMV coat protein, TMV coat protein, luteovirus replicase, MDMV messenger RNA, mutant geminiviral replicase, Umbellularia californica C12:0 preferring acyl-ACP thioesterase, plant C10 or C12:0 preferring acyl-ACP thioesterase, C14:0 preferring acyl-ACP thioesterase (luxD), plant synthase factor A, plant synthase factor B, 6-desaturase, protein having an enzymatic activity in the peroxysomal-oxidation of fatty acids in plant cells, acyl-CoA oxidase, 3-ketoacyl-CoA thiolase, lipase, maize acetyl-CoA-carboxylase, 5-enolpyruvylshikimate-3-phosphate synthase (EPSP), phosphinothricin acetyl transferase (BAR, PAT), CP4 protein, ACC deaminase, ribozyme, protein having posttranslational cleavage site, protein fusion consisting of a DNA-binding domain of Gal4 transcriptional activator and a transcriptional activation domain, a translational fusion of oleosin protein with protein of interest capable of targeting the fusion protein into the lipid phase, DHPS gene conferring sulfonamide resistance, bacterial nitrilase, 2,4-D monooxygenase, acetolactate synthase or acetohydroxyacid synthase (ALS, AHAS), polygalacturonase, bacterial nitrilase, fusion of amino terminal hydrophobic region of a mature phosphate translocator protein residing in the inner envelope membrane of the plastid with protein of interest to be targeted into said membrane etc.).

Any human or animal protein can be expressed using the system of the invention. Examples of such proteins of interest include inter alia the following proteins of pharmaceutical interest: immune response proteins (antibodies, single chain antibodies, T cell receptors etc.), antigens, colony stimulating factors, relaxins, polypeptide hormones, cytokines and their receptors, interferons, growth factors and coagulation factors, enzymatically active lysosomal enzyme, fibrinolytic polypeptides, blood clotting factors, trypsinogen, 1-antitrypsin (AAT), as well as function-conservative proteins like fusions, mutant versions and synthetic derivatives of the above proteins.

As shown by the Example and as explained above, the kits, mixtures, vectors, plants and plant cells are in particular useful for expression of polypeptides, in particular heterooligomeric polypeptides in plant.

Therefore, the invention relates in one embodiment to the use of a kit of the invention, or of a mixture of the invention, or of a PVX virus vector of the invention, or of a plant or plant cell of the invention, or of a plant of the invention, or of a mixture of *Agrobacterium* cells of the invention, for producing polypeptides, in particular heterooligomeric polypeptides.

The terms "movement protein(s)" or "MP(s)" is known to the skilled person and is understood as protein(s) required for cell-to-cell movement like the MP ORF in tobamoviruses.

The term "triple gene block proteins" or "TGB" is known to the skilled person and is understood as proteins required for cell-to-cell movement like the TGB ORFs in potexviruses.

The term "coat protein" is known to the skilled person and is understood as protein(s) building the virus coat.

FIGURE LEGEND

FIG. 1: shows the viral vector backbone dilemma. The individual viral vectors, either PVX or TMV (with identical backbone) cannot co-infect a single plant cell; they will segregate during systemic movement and express foreign genes only in separate patches on the leaves. RdRp: RNA-dependent RNA polymerase; CP: coat protein; ORF: open reading frame; MP: movement protein, TGB: triple gene block. Arrows indicate subgenomic promoters.

Figure 2:
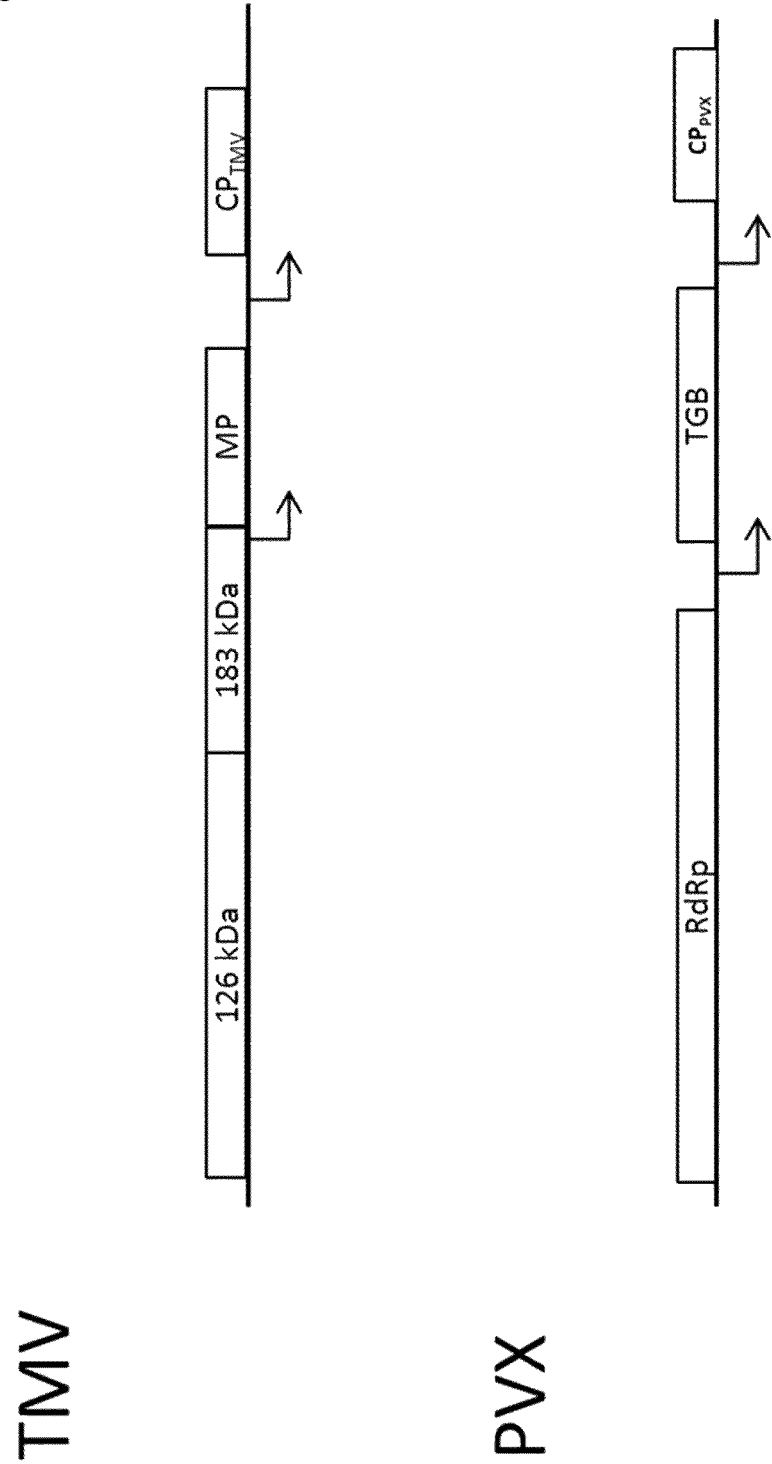

FIG. 2: shows the natural helping pair TMV and PVX. Both viruses can co-infect a single cell, move together and can systemically infect plants. RdRp: RNA-dependent RNA polymerase; CP: coat protein; ORF: open reading frame; MP: movement protein, TGB: triple gene block. Arrows indicate subgenomic promoters.

FIG. 3: shows a kit of the invention comprising a first and second plus strand viral vector. In these viral vectors, the coat proteins were exchanged reciprocally. Both viral can coinfect a single cell and can systemically infect plants. At the same time, neither one alone can systemically infect plants, ensuring containment. RdRp: RNA-dependent RNA polymerase; CP: coat protein; ORF: open reading frame; MP: movement protein, TGB: triple gene block. Arrows indicate subgenomic promoters. A: shows the complementing pair PVX-CP(TMV) and TMV-CP(PVX) with no additional ORFs inserted into the genome. B: one ORF is inserted in the PVX vector of the complementing pair, C: one ORF is inserted in the TMV vector of the complementing pair, D: ORF1 is inserted in the PVX vector and ORF2 in the TMV vector of the complementing pair.

FIG. 4: shows the schematic representation of a third viral vector of a kit of the present invention based on PVX. The viral vector does not comprise a coat protein; in particular the coat protein is completely deleted. Moreover, the viral vector comprises a heterologous ORF (PVX-ΔCP-ORFx). RdRp: RNA-dependent RNA polymerase; ORF: open reading frame; TGB: triple gene block. Arrows indicate subgenomic promoters.

FIG. 5: shows the schematic representation of a third viral vector of a kit of the present invention. The viral vector neither comprises a coat protein nor movement proteins. Moreover, the viral vector comprises a heterologous ORF (PVX-ΔCP-ΔTGB-ORFx). RdRp: RNA-dependent RNA polymerase; ORF: open reading frame. Arrows indicate subgenomic promoters.

Figure 6:
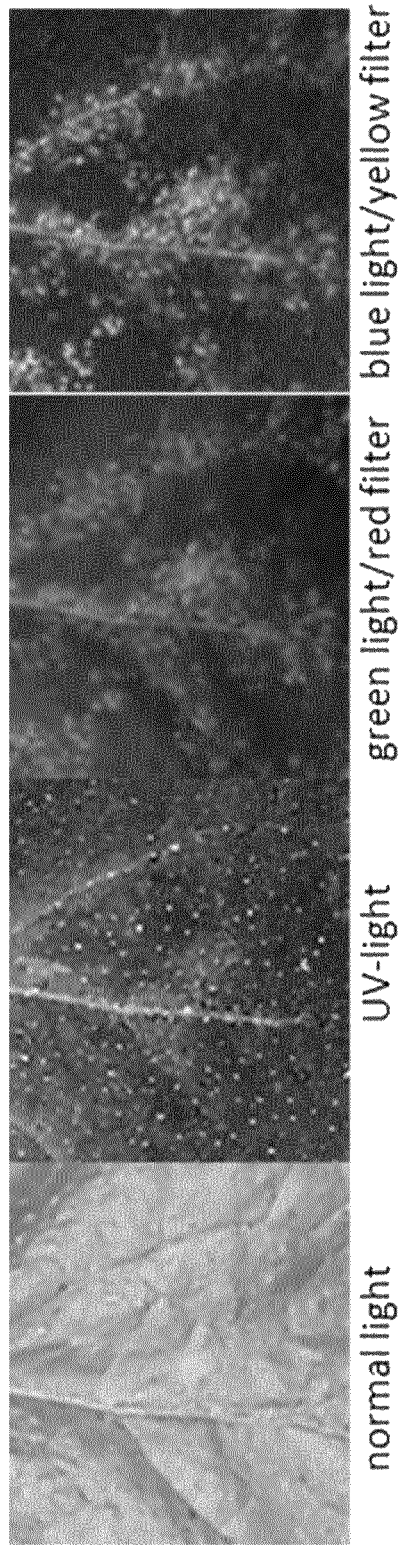
Figure 6:
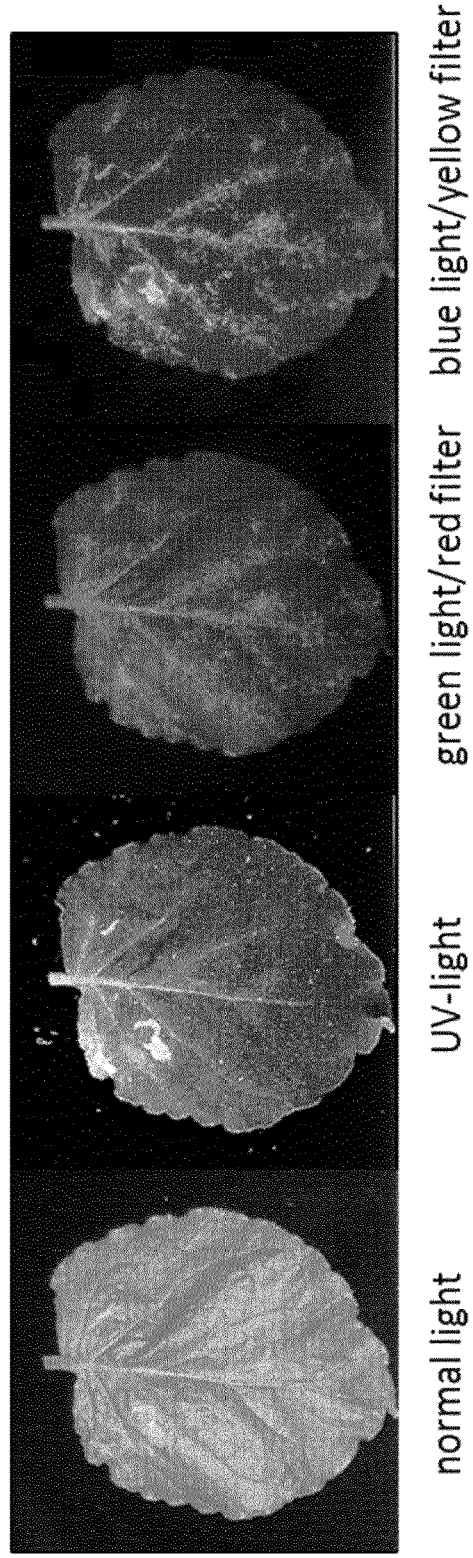

FIG. 6: shows in A and B a plant leaf from a systemically co-infected plant with the viral vectors PVX-mBananaΔCP, PVX-mCherry-CPTMV and TMV-GFP-CPPVX. Pictures were taken under normal light, UV-light for GFP, green light and red filter for mCherry and blue light and a yellow filter for mBanana visualization.

Figure 7:
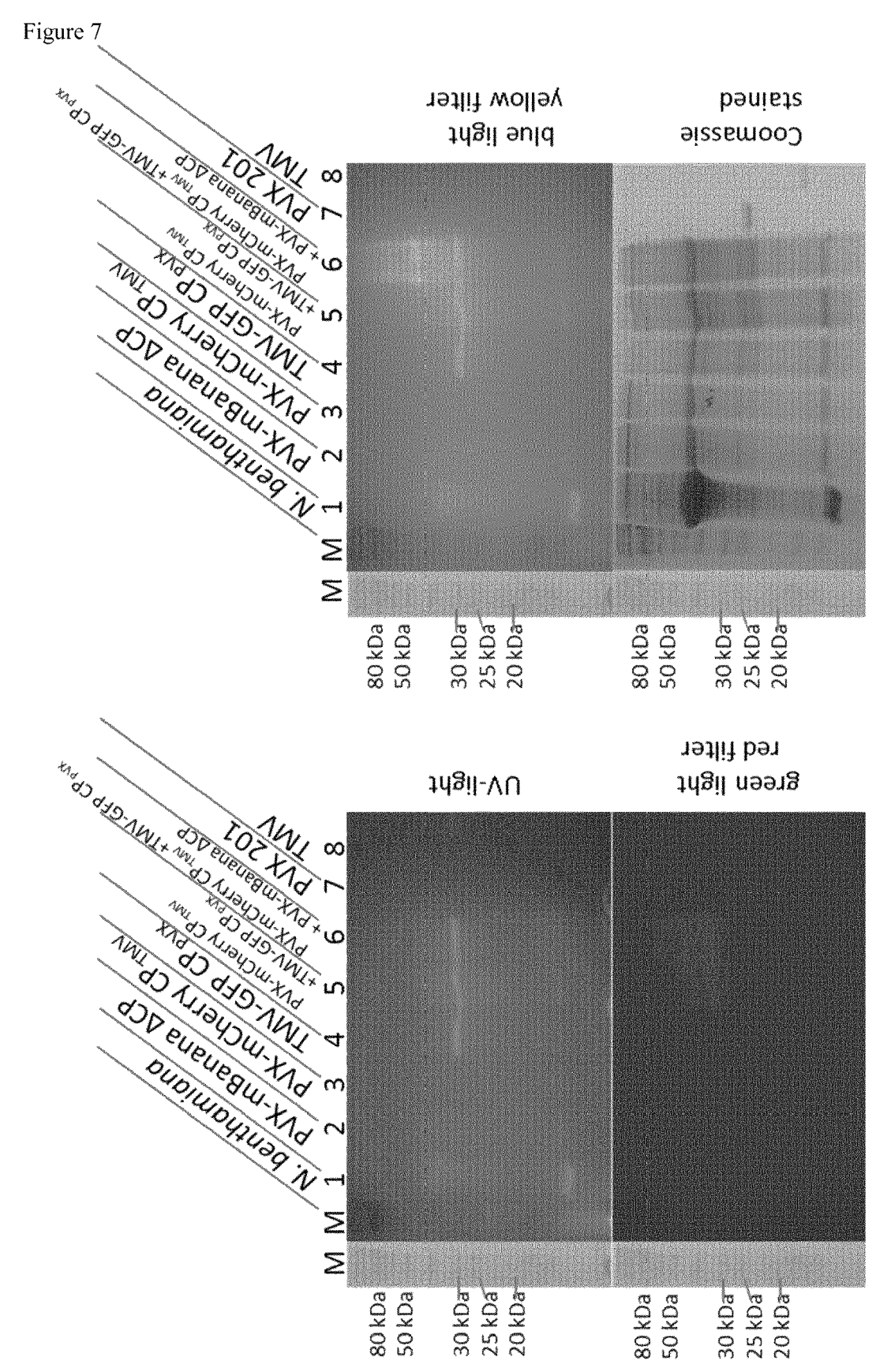

FIG. 7: shows SDS-PAGE of plant sap from leaves with the different viral vectors alone or in combination. For the SDS-PAGE the probes were not boiled to visualize the fluorescent proteins directly in the gel. The gel was observed under UV-light, green light and red filter, blue light and yellow filter before Coomassie staining and under normal light after Coomassie staining M: P7711S ladder (NEB); *N. benthamiana*: plant sap from a non infected/inoculated plant; PVX201: purified PVX201 particles (1 µg), TMV: purified TMV particles (1 µg).

Figure 8:
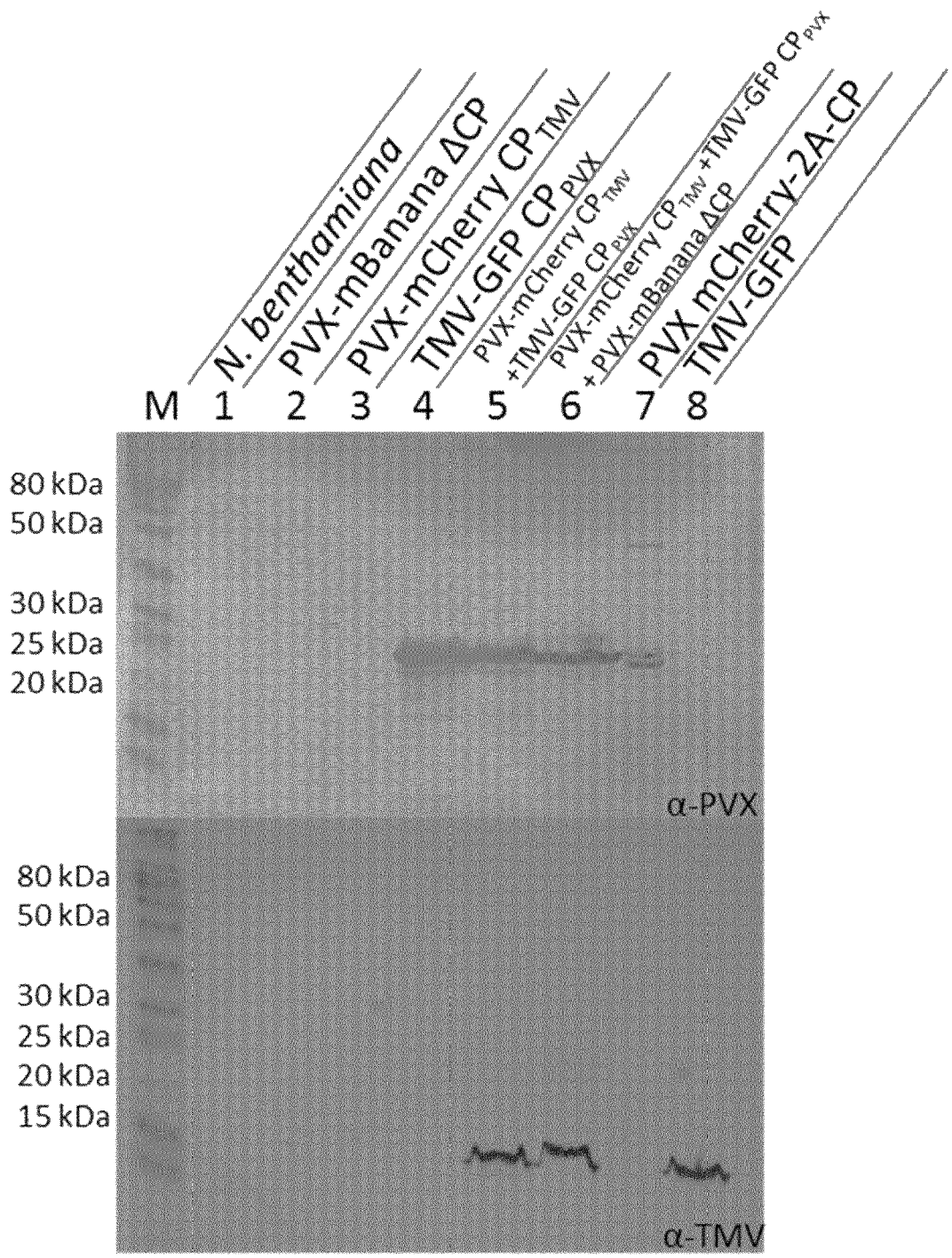

FIG. 8: shows Western blots of plant sap from leaves with the different viral vectors alone or in combination. For these analyses the probes were boiled before SDS-PAGE. Western blots were incubated with a polyclonal PVX or TMV antibody detecting the coat proteins, and a goat-anti-rabbit antibody labeled with an alkaline phosphatase. M: P7711S ladder (NEB); *N. benthamiana*: plant sap from a non infected/inoculated plant; PVX mCherry-2A-CP: plant sap from an infection with a mCherry-overcoat particle; TMV-GFP: plant sap from an infection with a TMV expression GFP.

Figure 9:
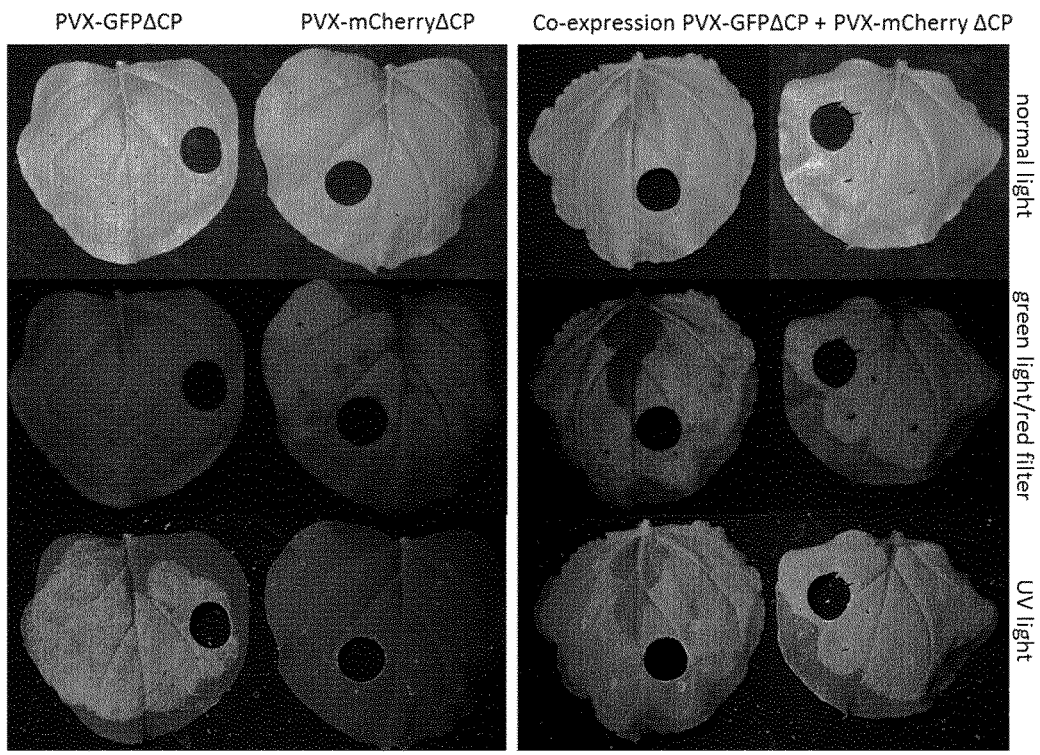

FIG. 9: shows *N. benthamiana* leaves expressing coat protein deficient PVX vectors. The leaves were inoculated with PVX-GFPΔCP, PVX-mCherryΔCP or both vectors. The pictures were taken at 4 days post inoculation (dpi).

Figure 10:
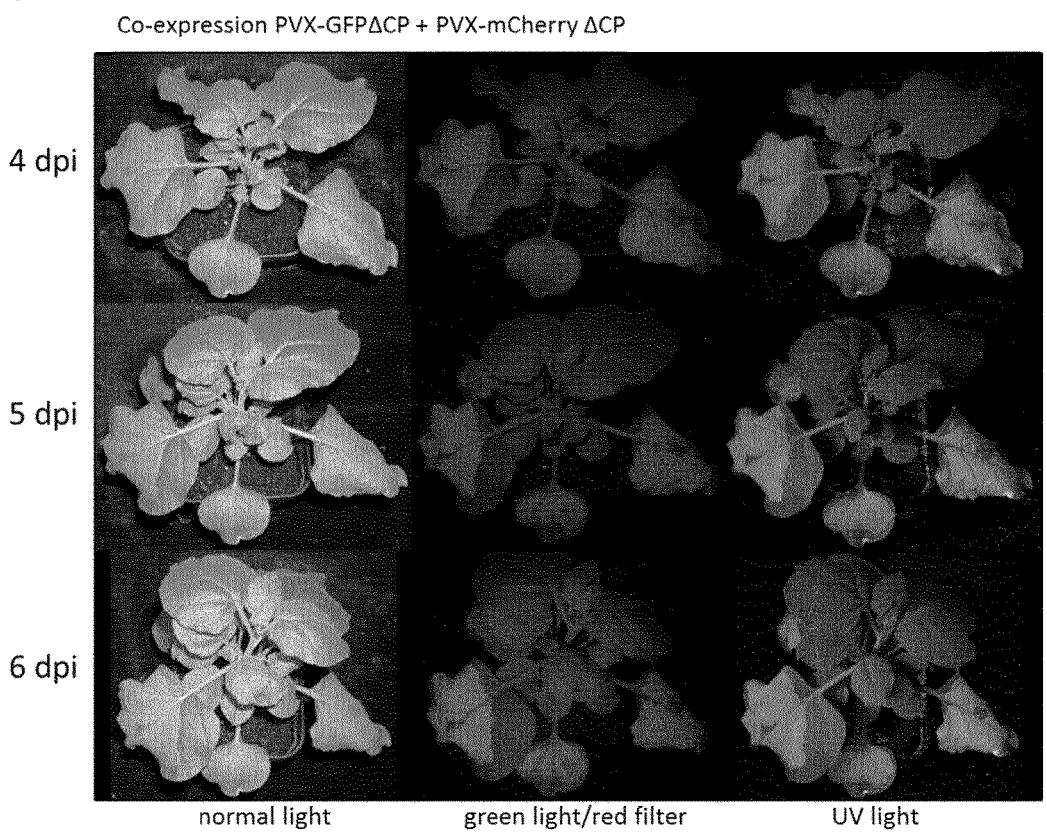

FIG. 10: shows *N. benthamiana* plant co-expressing PVX-GFPΔCP and PVX-mCherryΔCP. Pictures were taken at 4, 5 and 6 days post inoculation (dpi).

Figure 11:
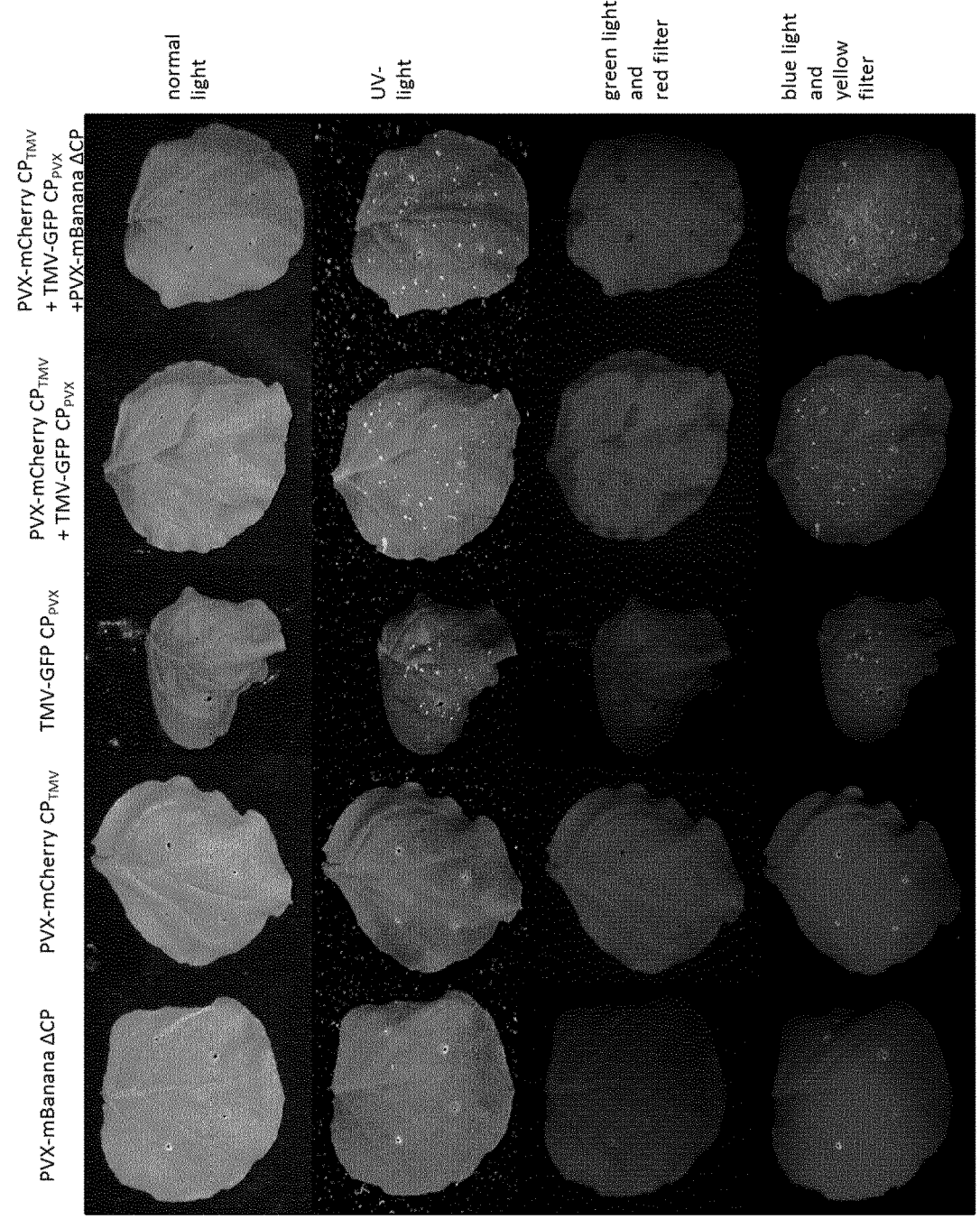

FIG. 11: shows inoculated leaves of *N. benthamiana* with the different viral vectors alone or in combination. Pictures were taken under normal light, UV-light for GFP, green light and red filter for mCherry and blue light and a yellow filter for mBanana visualization. The plant parts were harvested 13 days post inoculation (dpi).

Figure 12:
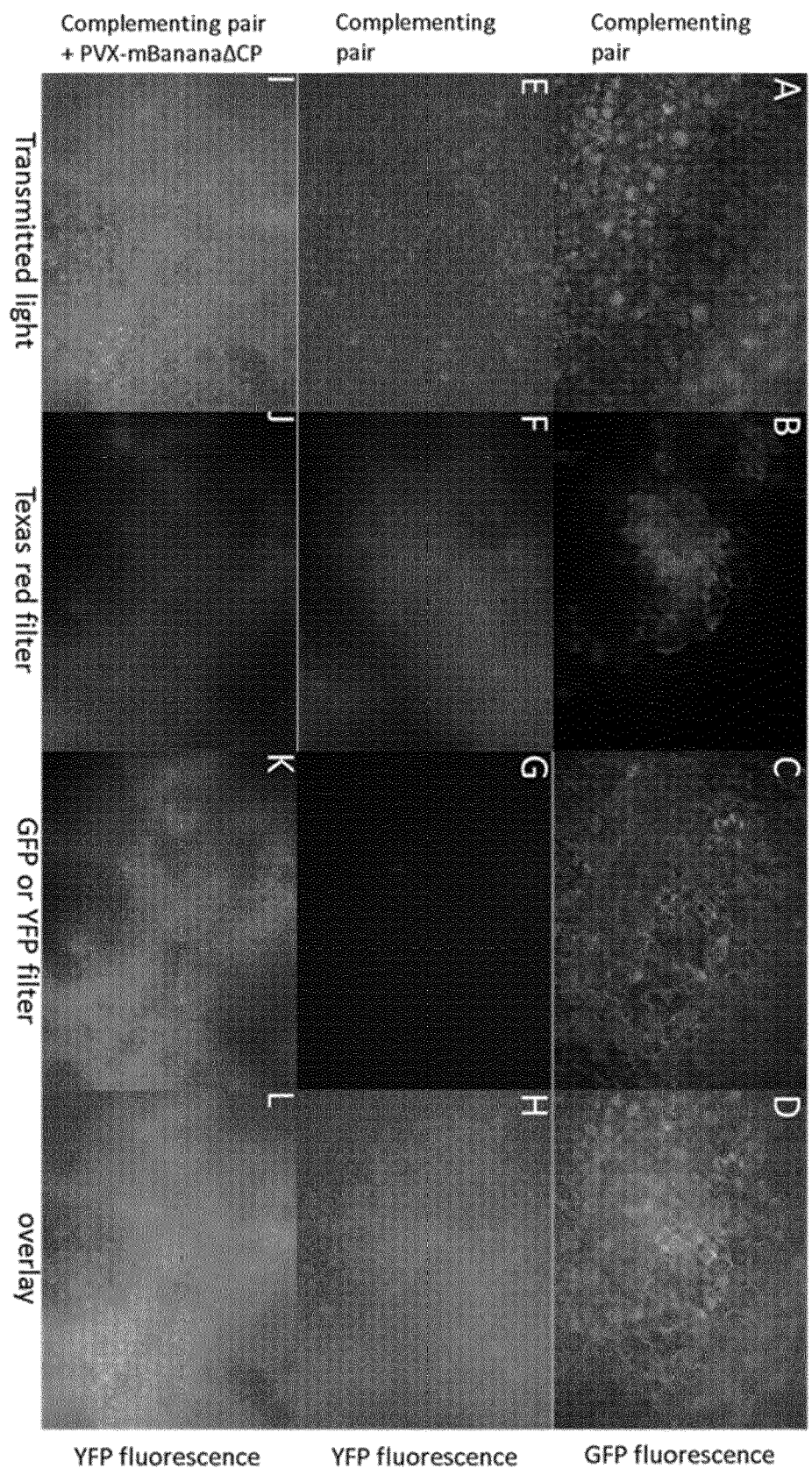

FIG. 12: shows microscopic pictures of plant leaves infected with the complementing pair with specific excitation of the fluorescent proteins. A-D: complementing pair with excitation of mCherry (Texas red filter) and GFP (GFP filter), E-H: complementing pair with excitation of mCherry and mBanana (YFP filter); I-L: complementing pair with PVX-mBananaΔCP with excitation of mCherry and mBanana; A, E, I: cells shown with transmitted light, B, F, J: excitation of mCherry, C: excitation of GFP, G, K: excitation of mBanana, D, H, L: overlay of pictures of the shown infection.

Figure 13:
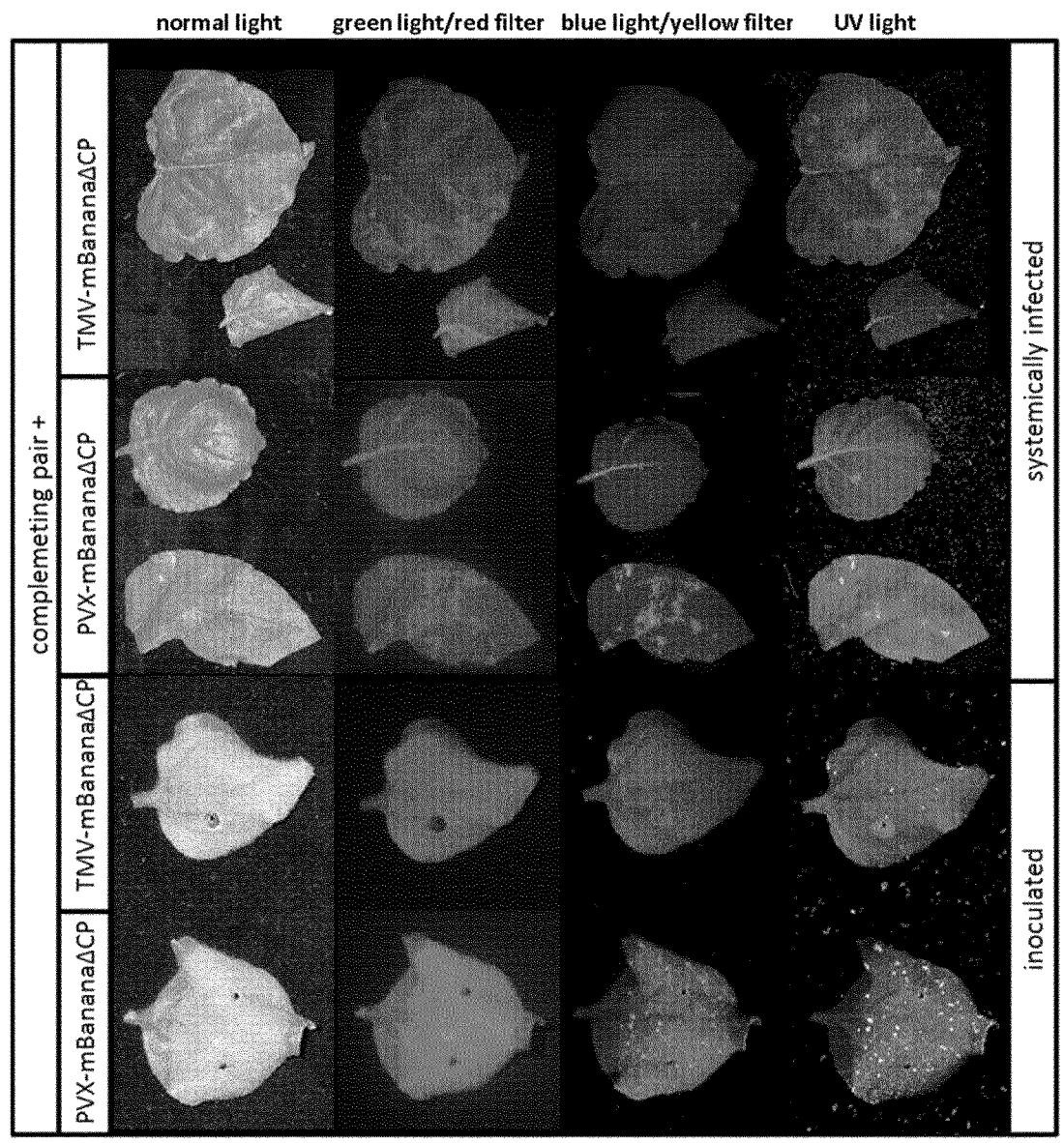

FIG. 13: shows plant leaves infected with the complementing pair and a third vector either PVX or TMV lacking a coat protein. Co-inoculations of the complementing pair PVX-mCherry-CPTMV and TMV-GFP-CPPVX were trialed with a third vector expressing mBanana, which was based either on PVX or TMV and is lacking a coat protein. Leaves are shown at 7 dpi (inoculated leaves) and at 24 dpi (systemically infected leaves) and the specific excitation conditions for the different fluorescent proteins were applied.

Figure 14:
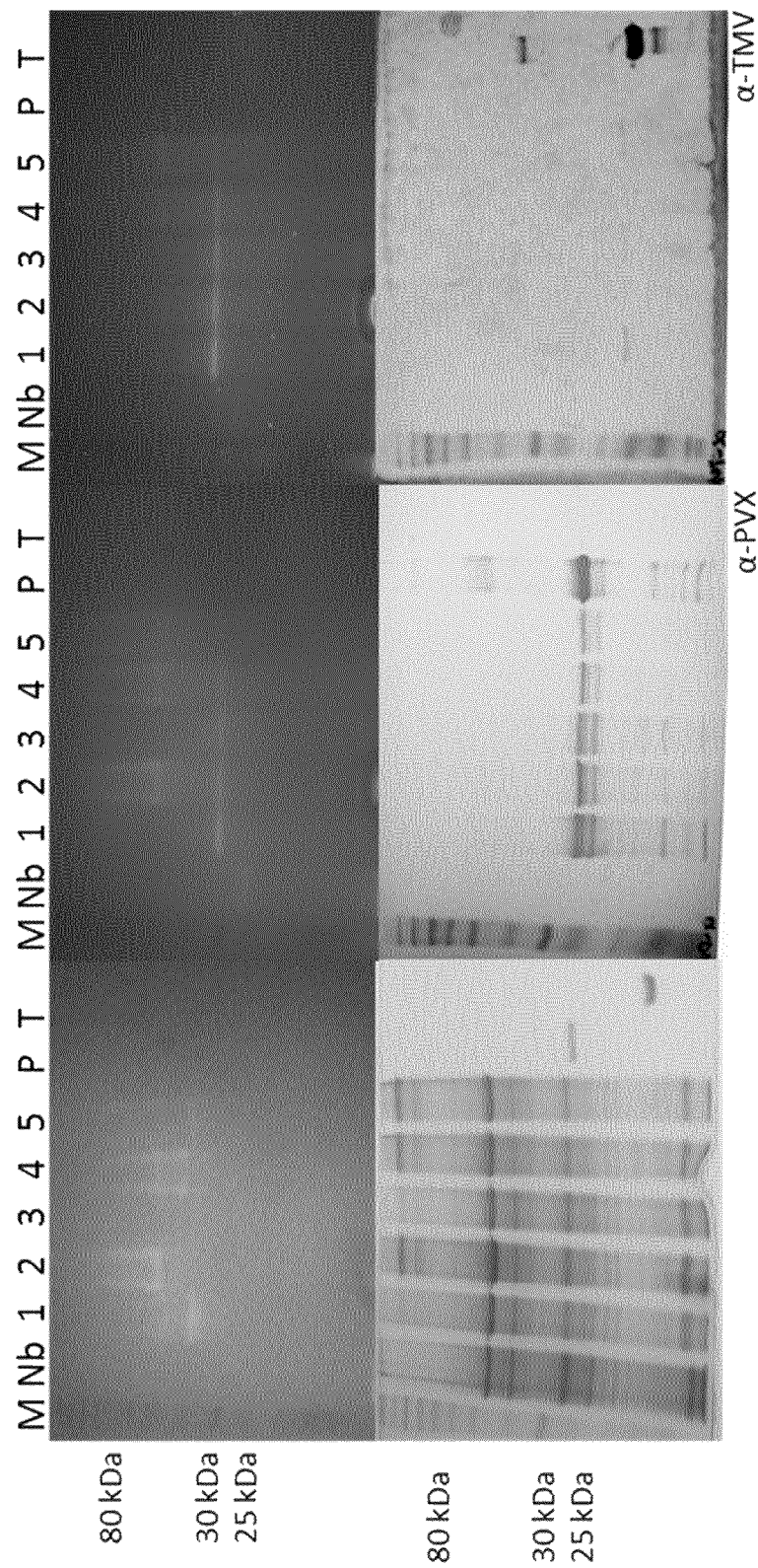

FIG. 14: shows an SDS-PAGE and Western blots of systemic infected leaves with the complementing pair and a third vector either PVX or TMV lacking a coat protein. The gels are shown under green light with a red filter (top left), blue light and a yellow filter (top middle) and under UV light (top right) before the Coomassie staining for the visualization of the fluorescent proteins. On the bottom the Coomassie stained gel (left), and Western blot against the CP of PVX (α-PVX) and the CP of TMV (α-TMV) are shown. M: P7711S protein ladder (NEB), Nb: *N. benthamiana* non infected plant, 1: complementing pair at 26 dpi, 2: complementing pair with PVX-mBananaΔCP at 26 dpi, 3: complementing pair at 33 dpi, 4: complementing pair with PVX-mBananaΔCP at 33 dpi, 5: complementing pair with TMV-mBananaΔCP at 33 dpi. P: PVX201 purification (1 µg), T: TMV purification (1 µg).

Figure 15:
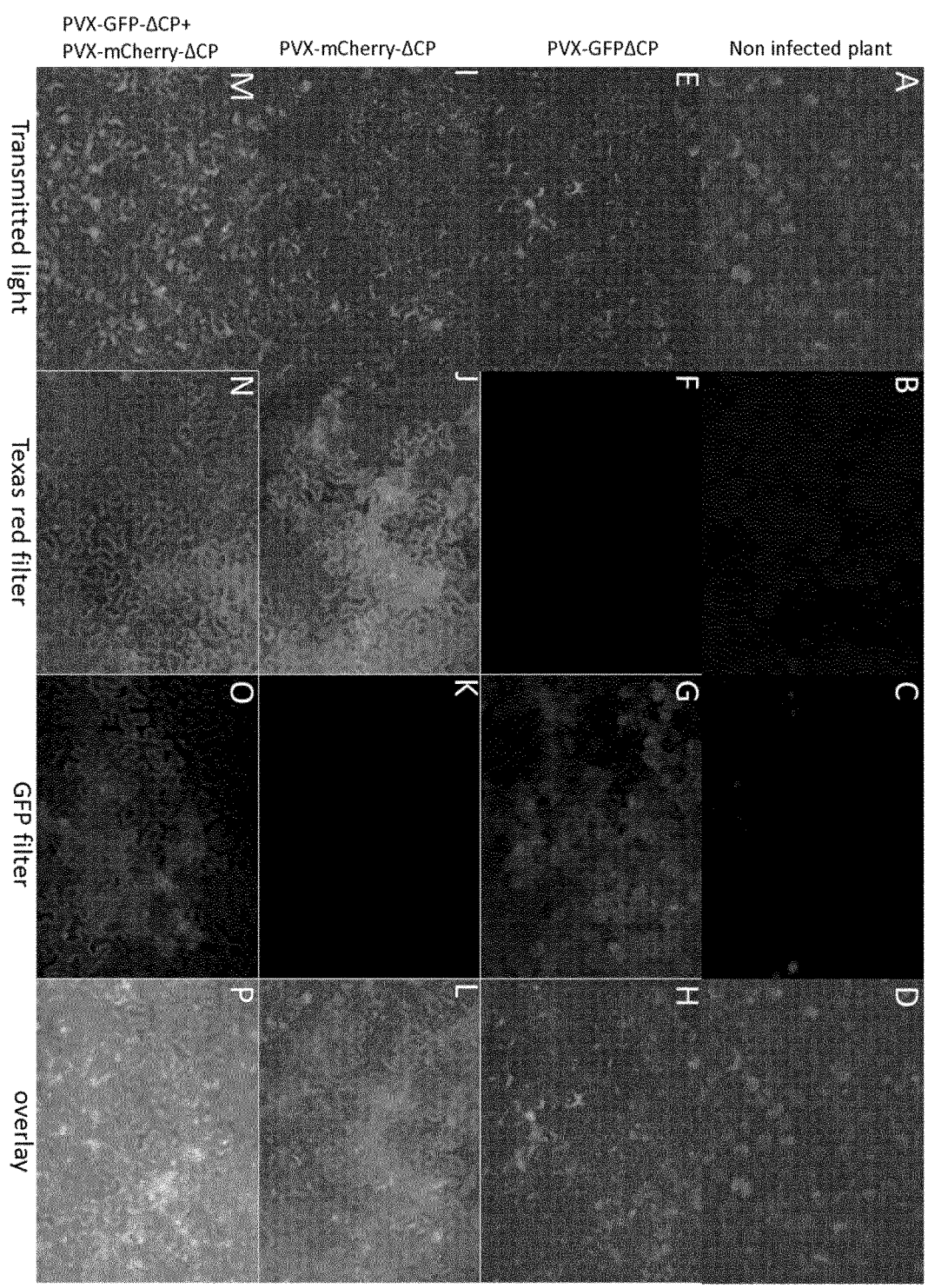

FIG. 15: shows microscopic pictures of plant leaves of infections with PVX based CP deficient vectors with excitation of the fluorescent proteins. A-D: *N. benthamiana* non infected plant. E-H: plant infected with PVX-GFPΔCP, I-L: plant infected with PVX-mCherryΔCP, M-P: plant co-infected with PVX-GFPΔCP and PVX-mCherryΔCP. A, E, I, M: cells show with transmitted light, B, F, J, N: excitation for mCherry (Texas red filter); C, G, K, O: excitation of GFP (GFP filter), D, H, L, P: overlay of the pictures of the shown infection.

EXAMPLES

Example 1

Generation of Vectors and Co-expression of Several Heterologous Proteins with Complementing Viral Vectors The complementation vectors were generated with help of the gene splicing by overlap extension (SOE) PCR method. For the construction of a PVX with the coat protein of TMV three PCR products were created. In PCR1 the mCherry gene was inserted into the PVX genome (PVX-mCherry) and the subgenomic promoter of the PVX coat protein was amplified with primers mCherry-ClaI and SOE-TMVCP rv including an overlapping sequence for the fusion. PCR2 amplified a part of the subgenomic promoter and the ORF of the TMV coat protein from the vector pJL24 (US 2010/0071085 A1) with primers SOE-TMVCP fw and SOE-TMVCP2 rv including two overlapping sequences, the 5'-end complementary to PCR product 1 and the 3'-end complementary to PCR product 3. With PCR 3 the 3' part of the PVX genome including parts of the plasmid backbone was created with primers SOE-TMVCP2-fw and M13 universe from the vector PVX-mCherry. In a fourth PCR lacking primers all PCR products were fused due to the overlapping sequences and again amplified in PCR 5 with the primers mCherry-ClaI and M13 universe. The final PCR product was then cut with ClaI and SalI and ligated into the PVX vector which was cut with the same enzymes and dephosporylated with a calf intestinal phosphatase (CIP). The PVX vector also consists of the plasmid backbone of the binary pTRAc vector (Mclean, 2007, J Gen Virol 88, 1460-1469). The PVX genome of the UK3 strain is integrated between left border and right border of the T-DNA. The subgenomic promoter of the coat protein is duplicated and a multiple cloning site with the restriction enzymes NheI, ClaI and SmaI is integrated (pPVX201 Patent WO96/12027). In the final vector construct pPVX-mCherry-CP$_{TMV}$ codes for the potexviral RNA-dependent RNA-polymerase and the triple gene block proteins, as well as the heterologous genes for the fluorescent protein mCherry and the coat protein of TMV. The subgenomic promoters for the expression of mCherry and the TMV coat protein are the duplicated sg promoters of the PVX coat protein.

TABLE 1

DNA oligomers used for construction of complementation vectors

| primer name | primer sequence (5'-3') |
|---|---|
| M13 universe | GTTGTAAAACGACGGCCAGT (SEQ ID No. 1) |
| mCherry-ClaI | TAGCATCGATATGGTGAGCAAG (SEQ ID No. 2) |
| PacI-GFP-TMV | TCATTAATTAAATGGCTAGC (SEQ ID No. 3) |
| SOE2-CPfw | AGTACGTTTTAATCAATATGTCAGCACCAGCTAG CAC (SEQ ID No. 4) |
| SOE2-CP-rv | TGCTAGCTGGTGCTGACATATTGATTAAAACGTA CTC (SEQ ID No. 5) |
| SOE2-CP-NotI-rv | AATAGCGGCCGCTATGGTGGTGGTAG (SEQ ID No. 6) |
| SOE-TMVCP-fw | ATTGATACTCGAAAGATGCCTTATACAATC (SEQ ID No. 7) |
| SOE-TMVCP-rv | ATTGTATAAGGCATCTTTCGAGTATCAATG (SEQ ID No. 8) |
| SOE-TMVCP2-fw | AACTCCGGCTACTTAACTACGTCTACATAAC (SEQ ID No. 9) |
| SOE-TMVCP2-rv | AGACGTAGTTAAGTAGCCGGAGTTG (SEQ ID No. 10) |

For the construction of a TMV vector two PCR products were created. In PCR 1 the sequence of the green fluorescent protein was amplified adding a PacI restriction site at the 5'-end and a part of coat protein subgenomic promoter of TMV with the primers PacI-GFP-TMV and SOE2-CP rv (Table 1) on the plasmid pJL24. In the second PCR the coat protein sequence of PVX was amplified with the primers SOE2-CP fw and SOE2-CP-NotI creating a construct with a part of the subgenomic promoter of TMV at the 5'-end and a NotI restriction site at the 3'-end. The two PCR products were fused in a third PCR without primers and amplified in a fourth PCR with the primers PacI-GFP-TMV and SOE2-CP NotI. The final PCR product was cut with the enzymes PacI and NotI and purified over an agarose gel. The target vector pTRBOG (US 2010/0071085 A1) was treated with the same restriction enzymes and dephosphorylated with CIP. The PCR fragment was ligated into the TMV vector and resulted in the plasmid pTMV-GFP-CP$_{PVX}$.

For the construction of PVX vectors with complete coat protein fusions existing PVX vectors with an N-terminal mBanana coat protein fusions with the 2A sequence were used. The PVX-mBanana-2A-CP for example is a PVX vector compatible for Agroinfection. The backbone of the plasmid is the binary pTRAc vector. The PVX genome of the UK3 strain is integrated between left border and right border of the T-DNA. The chosen vectors have a coat protein fusion of different fluorescent proteins with the 2A sequence of the Food and Mouth Disease Virus (FMDV), e.g. the yellow fluorescent protein mBanana. The 3' part of the PVX genome was amplified with a PCR and the restriction site BspEI which is also at the beginning of the 2A sequence in the fusion vectors was added to the 5' part with the primers 2ADelCPfw (5'-AATCCGGATAACTACGTCTA-CATAACCG-3' (SEQ ID No. 11)) and M13 universe (5'-GTTGTAAAACGACGGCCAGT-3' (SEQ ID No. 1)). The primer M13 universe binds inside the vector backbone outside the PVX genome and the primer 2ADelCpfw binds directly downstream of the coat protein coding sequence and adds the BspEI site. The product was subcloned into the pCR2.1-Topo vector (Lifetechnologies, Carlsbad, USA) amplified in E. coli SCS110 to create non methylated plasmid DNA. The pCR2.1 vector was cut with BspEI and XhoI. The target vectors with the coat protein fusions were treated with the same enzymes so the 2A sequence and the 3'-end of the PVX genome was deleted. The 3'-end without the complete coat protein sequence was then ligated into the PVX genome and confirmed by sequencing.

In the present invention a plant virus expression system with novel containment features was developed. In this system two different viral vectors complement a defective function of each other, by reciprocal coat protein exchange. By these means no viral vector alone can systemically infect a plant. In this example a TMV vector with GFP as functional heterologous ORF and the coat protein of PVX (representing the "second vector") and a PVX vector with mCherry as functional heterologous ORF and the CP of TMV (representing the "first vector") and a PVX vector with mBanana as functional heterologous ORF and with a complete deletion of the CP (representing a "third vector") were created.

The viral vectors were transformed into Agrobacterium tumefaciens strain GV3101:pMP90RK for PVX based vectors, and GV2260 for TMV based vectors. The Agrobacteria were grown at 26° C. in YEB media (0.5% beef extract, 0.1% yeast extract, 0.5% peptone, 0.5% sucrose, 2 mM MgSO4) with the antibiotics carbenicillin (100 mg/l), rifampicin (50 mg/l) and kanamycin (50 mg/l for GV3101 and 25 mg/l for GV2260). After 24 hours the cultures were supplemented with 10 µM MES (pH5.6), 10 µM glucose and 20 µM acetosyringone and incubated for another day. The cultures were then set to an OD$_{600}$=1 with 2×infiltration media (100 g/l sucrose, 3.6 g/l glucose, 8.6 g/l Murashige and Skoog (MS) salts, pH 5.6), supplemented with 200 µM acetosyringone and incubated for 30 minutes at room temperature. For co-inoculation of two or more different constructs the cultures were mixed so each culture would have an OD$_{600}$ of 1. The mixtures were inoculated into ca. 4 weeks old N. benthamiana leaves with a syringe without needle. The plants were further incubated in a phytochamber with constant light (25000-30000 lux) at 26° C. for 12 h and 12 h 20° C. in the dark.

The plants were monitored each day under the specific conditions for the chosen fluorescent protein (Table 2). For GFP visualization a handheld UV lamp (7000 µW, Novodirect, Kehl/Rhein, Germany), for mCherry a green LCD lamp (KL2500, Leica, Wetzlar, Germany) and for mBanana a high intensity blue LED lamp (Optimax™450 Spectroline, Spectronics corporation, New York, USA) was used. Pictures were taken with a Nikon Coolpix 5400 camera (Nikon Deutschland, Dusseldorf, Germany).

TABLE 2

| Fluorescent protein | Excitation maximum (nm) | Excitation method | Emission maximum (nm) |
|---|---|---|---|
| GFP | 395/475 | UV lamp (260 nm) | 508 |
| mCherry | 587 | green lamp (515 nm) | 610 |
| mBanana | 540 | Blue lamp (450 nm) | 553 |

In FIG. 11, inoculated leaves are shown that express the viral vectors PVX-mBananaΔCP, PVX-mCherry-CPTMV, TMV-GFP-CPPVX, and their combinations. The TMV vector is still capable of cell-to-cell movement without its coat protein, so the inoculated leaf shows already a good expression of GFP. In the combination of the vectors with a complementation of the coat protein from the other virus the effect is already visible in the inoculated leaf. The PVX vectors express their heterologous ORF stronger in combination with the TMV vector. Surprisingly also a second PVX vector (mBanana) lacking a coat protein is expressed clearly in the same cells as the first PVX vector (mCherry).

After 26 dpi the plants were systemically infected with the two or even three different viral vectors. This demonstrates the ability of the viral vectors to complement each others innate coat protein deficiencies and secondly support systemic movement of further defective viral vectors.

In FIGS. 6 A and B, a leaf from a systemically infected plant co-inoculated with the viral vectors TMV-GFP-$CP_{PVX}$ and PVX-mCherry-$CP_{TMV}$ plus PVX-mBananaΔCP is shown.

For the isolation of total soluble proteins the leaves were harvested at different time points and homogenized with two volumes PBS (pH 7.4). Insoluble plant parts were separated during centrifugation at 13000 rpm for 10 min at 4° C. The total amount of soluble proteins was measured with a Bradford assay using Roti®Quant reagent (Roth, Karlsruhe, Germany).

For the quantification of fluorescence isolated total soluble protein was used. 50 μg of total protein were diluted in 100 μl of PBS and fluorescence profiles were measured in a microtiter plate reader (ELISA-Reader Infinite M200, TECAN Group Ltd, Männedorf, Switzerland). Fluorescent proteins were also visualized in SDS gels before Coomassie Brilliant Blue staining.

For protein analysis discontinuous SDS-PAGE and Western blotting was used. The plant sap was supplemented with 5× reducing sample buffer (62.5 mM Tris-HCl pH 6.8, 30% glycin, 4% SDS, 10% 2-mercaptoethanol, 0.05% bromophenol blue) and directly loaded on the gels for visualization of fluorescence in the gels or boiled for 5-10 minutes for Western blotting. The probes were then loaded onto a 12% SDS gel and after electrophoresis either stained with Coomassie Brilliant Blue or blotted on a nitrocellulose membrane for Western blot analysis. The membranes were blocked for 1 h with 5% skimmed milk in PBS and then incubated with a polyclonal antibody against the coat protein of PVX (DSMZ, Braunschweig, Germany) or TMV (Bioreba A G, Reinach, Switzerland) for at least 2 h at room temperature. As secondary antibody a monoclonal alkaline phosphatase-conjugated goat anti-rabbit antibody (Dianova, Hamburg, Germany) was used and the signal was visualized with nitroblue tetrazolium chloride/5-bromo-4-chloro-3'-indolyphosphate p-toluidine salt (NBT/BCIP) (Roth, Karlsruhe, Germany).

In SDS-PAGEs the successful co-expression of the heterologous proteins was confirmed again (FIG. 7). The different fluorescent proteins are easily visible under specific excitation in the plant sap from co-infected leaves. For mCherry and mBanana a dimerization of these two fluorescent proteins is also visible forming a protein band twice the size of a protein monomer. The expression of the different coat proteins from the viral vectors and the lack of their own innate coat protein were proven in Western Blot analysis with polyclonal antibodies against the TMV or PVX coat protein (FIG. 8).

These data confirm the lack of the own coat protein in the viruses and the expression of the foreign coat protein as well as a heterologous complementation of the coat protein function in co-infections.

To confirm the co-expression of mCherry and mBanana by two different PVX based vectors in the same cells, the infected leaves were analyzed with the fluorescence microscope Biorevo BZ-9000 (Keyence, Neu-Isenburg, Germany). The leaves infected with the complementing pair showed a clear co-expression of mCherry and GFP in the same cells (FIG. 12 A-D) and gave no signal with the excitation for mBanana (E-H). In leaves co-infected with the complementing pair and PVX-mBananaΔCP and clear co-expression of mBanana and mCherry can be seen (I-L). A GFP expression in these regions was also confirmed (data not shown).

We further analyzed if also a second TMV vector with a deficient CP gene can co-infect the plants with our complementing pair. However, the infection only showed a co-expression of two different PVX-based vectors in infected leaves (FIG. 13). Infiltrated leaves at first sight seemed to co-express either the complementing pair with a third TMV or PVX vector, because an mBanana expression could be observed in all infiltrated leaves. In systemically infected leaves only the combination with the additional PVX vector showed a co-expression of all three fluorescent proteins. In the combination with TMV-mBananaΔCP vector only the complementing pair could be seen in the same areas. Very rare spots of an mBanana expression could be seen in this combination, which never overlay with the GFP expression. Thus, the $CP_{TMV}$ expressed by PVX could complement the CP deficient TMV vector and allowed a spread out of the inoculated leave, but a co-infection of two different TMV-based vectors was not observed.

These findings were confirmed in SDS-PAGE and Western blot analysis (FIG. 14). The visualization of fluorescent proteins in the gels showed a co-expression of mCherry and GFP by the complementing pair in systemic infected leaves and a co-expression of mBanana in co-infections with the PVX-mBananaΔCP vector. Furthermore a dimerization of the mCherry and mBanana was observed when they are co-expressed, without mBanana in the cells mCherry showed a lower band in the gels. In plants infected with the additional TMV-mBananaΔCP small amounts of mBanana can be found in the leaves with a reduced amount of GFP and mCherry in these leaves. This can be explained by the missing co-expression of these vectors. The complementing pair co-expresses GFP and mCherry in these leaves but is separated from the second TMV vector expressing mBanana, which leads to an overall lowered amount of expressed recombinant proteins. The Western blots confirmed the expression of the CPs of the viral vectors by the complementing pair.

In summary we could confirm the co-expression of the complementing pair with an additional PVX-based vector lacking the coat protein, whereas a second TMV vector was not able to co-infect the plants with the complementing pair. With these vectors we are the first to show a co-expression of two viral vectors based on the same RNA virus in systemic infected leaves.

The capability of coat protein complementation enabling systemic movement and the simultaneous production of recombinant proteins and at the same time ensuring a biosafety containment clearly show the benefit of the invention.

Example 2

Protein Production with Movement-deficient PVX Vectors

For the expression of two or more recombinant proteins with viral vectors derived from one virus species, Potato Virus X (PVX) vectors were constructed which are lacking the coat protein. In these vectors the entire coat protein open reading frame was deleted, in contrast to known vectors were a part of the C-terminal coding region of the coat protein was preserved.

The viral vectors were transformed into *Agrobacterium tumefaciens* strain GV3101:pMP90RK and grown at 26° C. in YEB media (0.5% beef extract, 0.1% yeast extract, 0.5% peptone, 0.5% sucrose, 2 mM $MgSO_4$) with the antibiotics carbenicillin (100 mg/l), rifampicin (50 mg/l) and kanamycin (50 mg/l). After 24 hours the cultures were supplemented with 10 µM MES (pH5.6), 10 µM glucose and 20 µM acetosyringone and incubated for another day. The cultures were then set to an $OD_{600}=1$ with 2×infiltration media (100 g/l sucrose, 3.6 g/l glucose, 8.6 g/l Murashige and Skoog (MS) salts, pH 5.6), supplemented with 200 µM acetosyringone and incubated for 30 minutes at room temperature. For co-inoculation of two or more different constructs the cultures were mixed so each culture would have an $OD_{600}$ of 1. The mixtures were inoculated into ca. 4 weeks old *N. benthamiana* leaves with a syringe without needle. The plants were further incubated in a phytochamber with constant light (25000-30000 lux) at 26° C. for 12 h and 12 h 20° C. in the dark.

The plants were monitored each day under the specific conditions for the chosen fluorescent protein (Table 3). For GFP visualization a handheld UV lamp (7000 µW, Novodirect, Kehl/Rhein, Germany), for mCherry a green LCD lamp (KL2500, Leica, Wetzlar, Germany) was used. Pictures were taken with a Nikon Coolpix 5400 camera (Nikon Deutschland, Dusseldorf, Germany).

TABLE 3

| fluorescent protein | excitation maximum (nm) | used excitation method | emission maximum (nm) | observation |
|---|---|---|---|---|
| GFP | 395/475 | UV lamp (260 nm) | 508 | |
| mCherry | 587 | green lamp (515 nm) | 610 | red filter |

The results clearly show that the C-terminal coding region of the coat protein is not strictly required for the replication of the PVX vector. GFP and mCherry are produced in the inoculated plant cells (FIG. 9). In co-inoculated leaves a co-expression of the two different recombinant proteins is clearly visible and proven on the cellular level in microscopic studies (data not shown).

At 4 days post inoculation a good co-expression of both fluorescent proteins was visible and the expression reached the best co-expression levels at 6 dpi for this enzyme combination (FIG. 10). However due to different requirements of different recombinant proteins other production times are also possible and/or suitable.

For the isolation of total soluble proteins the leaves were harvested at different time points and homogenized with two volumes PBS (pH 7.4). Insoluble plant parts were separated during centrifugation at 13000 rpm for 10 min at 4° C. The total amount of soluble proteins was measured with a Bradford assay using Roti®Quant reagent (Roth, Karlsruhe, Germany).

For the quantification of fluorescence isolated total soluble protein was used. 50 µg of total proteins were diluted in 100 µl of PBS and fluorescence profiles were measured in a microtiter plate reader (ELISA-Reader Infinite M200, TECAN Group Ltd, Männedorf, Switzerland). Fluorescent proteins were also visualized in SDS gels before Coomassie Brilliant Blue staining.

For protein analysis discontinuous SDS-PAGE and Western blotting was used (Laemmli, 1970). The plant sap was supplemented with 5× reducing sample buffer (62.5 mM Tris-HCl pH 6.8, 30% glycin, 4% SDS, 10% 2-mercaptoethanol, 0.05% bromophenol blue) and directly loaded on the gels for visualization of fluorescence in the gels or boiled for 5-10 minutes for Western blotting. The probes were then loaded onto a 12% SDS gel and after electrophoresis either stained with Coomassie Brilliant Blue or blotted on a nitrocellulose membrane for Western blot analysis. The membranes were blocked for 1 h with 5% skimmed milk in PBS and then incubated with a polyclonal antibody against the coat protein of PVX (DSMZ, Braunschweig, Germany) for at least 2 h at room temperature. As second antibody a monoclonal alkaline phosphatase-conjugated goat anti-rabbit antibody (Dianova, Hamburg, Germany) was used and the signal was visualized with nitroblue tetrazolium chloride/5-bromo-4-chloro-3'-indolyphosphate p-toluidine salt (NBT/BCIP) (Roth, Karlsruhe, Germany).

With SDS-PAGE and Western blot analysis it could be proven, that the PVX vectors express no coat protein (data not shown). Although former publications indicate the demand for the C-terminal coding region of the coat protein for the replication of the PVX vector, here it could be shown that the coat protein coding sequence can be completely deleted. On the contrary a good co-expression of two different and potentially more PVXΔCP vectors could be shown.

To confirm the co-expression of two different PVX based vectors in the same cells the infected leaves were analyzed with the fluorescence microscope Biorevo BZ-9000 (Keyence, Neu-Isenburg, Germany). The pictures confirmed no signals for the non-infected *N. benthamiana* plant (FIG. 15 A-D). In infections with PVX-GFPΔCP or PVX-mCherryΔCP only the expressed fluorescent protein could be seen (E-H for GFP, I-L for mCherry). In co-infections of these vectors a co-expression of the different fluorescent proteins can be observed in identical cells (M-P).

In summary, we could confirm the co-expression of different PVX-based vectors lacking its CP in agroinfiltrated leaves. This findings show that PVX vectors are capable of co-infections after knockout of CP functions. This is in contrast to the aforementioned known PVX-based vectors and also to TMV-based vectors, which are not capable of co-infections even after deletion of the MP and CP genes in the vectors (Julve et al., 2013).

Due to the coat protein deletion, containment is ensured. Moreover, the present invention overcomes the incompatibility of two or more vectors in one cell and therefore allows simultaneous expression of two or more heterologous ORFs located on different viral vectors in the same plant cells.

LITERATURE

Fedorkin, O. N., Merits, A., Lucchesi, J., Solovyev, A. G., Saarma, M., Morozov, S. Y., Makinen, K., 2000. Complementation of the movement-deficient mutations in potato virus X: potyvirus coat protein mediates cell-to-cell trafficking of C-terminal truncation but not deletion mutant of potexvirus coat protein. Virology 270, 31-42.

Julve, J. M., Gandia, A., Fernandez-Del-Carmen, A., Sarrion-Perdigones, A., Castelijns, B., Granell, A., Orzaez, D., 2013. A coat-independent superinfection exclusion rapidly imposed in *Nicotiana benthamiana* cells by tobacco mosaic virus is not prevented by depletion of the movement protein. Plant Mol Biol 81, 553-564.

Komarova, T. V., Skulachev, M. V., Zvereva, A. S., Schwartz, A. M., Dorokhov, Y. L., Atabekov, J. G., 2006. New viral vector for efficient production of target proteins in plants. Biochemistry (Mosc) 71, 846-850.

Laemmli, U. K., 1970. Cleavage of structural proteins during the assembly of the head of bacteriophage T4. Nature 227, 680-685.

The invention claimed is:

1. A kit comprising
   a) a first plus-sense single stranded ribonucleic acid (RNA) viral vector, and
   b) a second plus-sense single stranded RNA viral vector, wherein
   (i) the first plus-sense single-stranded viral vector and the second plus-sense single-stranded viral vector are derived from different plant viruses, and
   (ii) the coat protein open reading frame (ORF) of the virus from which the first vector is derived is completely deleted in the first plus-sense single stranded RNA viral vector, and
   (iii) the coat protein ORF of the virus from which the second vector is derived is completely deleted in the second plus-sense single stranded RNA viral vector, and
   (iv) the first plus-sense single stranded RNA viral vector comprises a functional coat protein ORF of the virus from which the second plus-sense single-stranded viral vector is derived, and
   (v) the second plus-sense single stranded RNA viral vector comprises a functional coat protein ORF of the virus from which the first plus- sense single-stranded viral vector is derived, and
   (vi) the first plus-sense single-stranded viral vector and the second plus-sense single-stranded viral vector comprise an RNA replicon which is able to replicate in plant cells, and wherein the virus from which the first plus-sense single-stranded viral vector is derived is a Potexvirus, and the virus from which the second plus-sense single-stranded viral vector is derived is a Tobamovirus.

2. The kit according to claim 1, wherein
   a) the functional coat protein ORF of the virus from which the second plus-sense single- stranded viral vector is derived is inserted at the location from which the coat protein ORF of the first plus-sense single-stranded viral vector is deleted, and/or b) the functional coat protein ORF of the virus from which the first plus-sense single- stranded viral vector is derived is inserted at the location from which the coat protein ORF of the second plus-sense single-stranded viral vector is deleted.

3. The kit according to claim 1, wherein
the first plus-sense single-stranded viral vector comprises a functional heterologous ORF in addition to the functional coat protein ORF or the second plus-sense single-stranded viral vector comprises a functional heterologous ORF in addition to the functional coat protein ORF.

4. The kit according to claim 1, wherein the kit further comprises
at least one additional plus-sense single stranded RNA viral vector, wherein
(i) the at least one additional plus-sense single-stranded viral vector comprises at least one functional heterologous ORF, and
(ii) the at least one additional plus-sense single-stranded viral vector is derived from a Potexvirus.

5. The kit according to claim 4, wherein the at least one additional plus-sense single stranded RNA viral vector is devoid of a functional movement protein ORF(s) of the Potexvirus.

6. A mixture comprising:
a) at least one first plus-sense single stranded RNA viral vector,
b) at least one second plus-sense single stranded RNA viral vector, and, optionally,
c) at least one third plus-sense single stranded RNA viral vector,
wherein
(i) the first plus-sense single-stranded viral vector and the second plus-sense single-stranded viral vector are derived from different plant viruses, and
(ii) the coat protein ORF of the virus from which the first vector is derived is completely deleted in the first plus-sense single stranded RNA viral vector, and
(iii) the coat protein ORF of the virus from which the second vector is derived is completely deleted in the second plus-sense single stranded RNA viral vector, and
(iv) the first plus-sense single stranded RNA viral vector comprises a functional coat protein ORF of the virus from which the second plus-sense single-stranded viral vector is derived, and
(v) the second plus-sense single stranded RNA viral vector comprises a functional coat protein ORF of the virus from which the first plus-sense single-stranded viral vector is derived, and
(vi) the first plus-sense single-stranded viral vector and the second plus-sense single-stranded viral vector comprise an RNA replicon which is able to replicate in plant cells, and
wherein
the virus from which the first plus-sense single-stranded viral vector is derived is a Potexvirus,
the virus from which the second plus-sense single-stranded viral vector is derived is a Tobamovirus, and
the at least one third plus-sense single-stranded viral vector is derived from a Potexvirus.

7. The mixture according to claim 6, comprising
(i) the at least one first plus-sense single stranded RNA viral vector, and
(ii) the at least one second plus-sense single stranded RNA viral vector, and
(iii) the at least one third plus-sense single stranded RNA viral vector.

8. A plant or plant cell
comprising at least one first plus-sense single stranded RNA viral vector and at least one second plus-sense single stranded RNA viral vector, and, optionally, at least one third plus-sense single stranded RNA viral vector(s),
wherein
(i) the first plus-sense single-stranded viral vector and the second plus-sense single-stranded viral vector are derived from different plant viruses, and
(ii) the coat protein ORF of the virus from which the first vector is derived is completely deleted in the first plus-sense single stranded RNA viral vector, and
(iii) the coat protein ORF of the virus from which the second vector is derived is completely deleted in the second plus-sense single stranded RNA viral vector, and
(iv) the first plus-sense single stranded RNA viral vector comprises a functional coat protein ORF of the virus from which the second plus-sense single-stranded viral vector is derived, and
(v) the second plus-sense single stranded RNA viral vector comprises a functional coat protein ORF of the virus from which the first plus-sense single-stranded viral vector is derived, and
(vi) the first plus-sense single-stranded viral vector and the second plus-sense single-stranded viral vector comprise an RNA replicon which is able to replicate in plant cells, and
wherein
the virus from which the first plus-sense single-stranded viral vector is derived is a Potexvirus, and
the virus from which the second plus-sense single-stranded viral vector is derived is a Tobamovirus, and
the at least one third plus-sense single-stranded viral vector is derived from a Potexvirus.

9. The plant according to claim 8, wherein more than one plant cell in more than one tissue of the plant
comprises the at least one first plus-sense single stranded RNA viral vector and the at least one second plus-sense single stranded RNA vector, and, optionally, the at least one third plus-sense single stranded RNA viral vector(s).

10. A method for producing in a plant, or-plant tissue, or plant cell a heterooligomeric polypeptide and/or two or more polypeptides, comprising providing to at least one plant cell
a) at least one first plus-sense single stranded RNA viral vector, and
b) at least one second plus-sense single stranded RNA viral vector, and
c) optionally, at least one third plus-sense single stranded RNA viral vector,
wherein
(i) the first plus-sense single-stranded viral vector and the second plus-sense single-stranded viral vector are derived from different plant viruses, and
(ii) the coat protein ORF of the virus from which the first vector is derived is completely deleted in the first plus-sense single stranded RNA viral vector, and (iii) the coat protein ORF of the virus from which the second vector is derived is completely deleted in the second plus-sense single stranded RNA viral vector, and (iv) the first plus-sense single stranded RNA viral vector comprises a functional coat protein ORF of the virus from which the second plus-sense single-stranded viral vector is derived, and (v) the second plus-sense single stranded RNA viral vector comprises a functional coat protein ORF of the virus from which the first plus-sense single-stranded viral vector is derived, and (vi) the first plus-sense single-stranded viral vector and the second plus-sense single-stranded viral vector comprise an RNA replicon which is able to replicate in plant cells, and (vii) the at least one plus-sense single stranded RNA viral vector and the at least one second plus-sense single stranded RNA viral vector comprise different heterologous ORFs, and wherein the virus from which the first plus-sense single-stranded viral vector is derived is a Potexvirus, and the virus from which the second plus-sense single-stranded viral vector is derived is a Tobamovirus, and the at least one third plus-sense single-stranded viral vector is derived from a Potexvirus.

11. The method of claim 10, a) further comprising isolating the heterooligomeric polypeptide and/or two or more polypeptides from the plant, plant tissue, or plant cell, and/or b) wherein systemic infection of the plant is achieved, and/or c) wherein the heterooligomeric polypeptide is an immunoglobulin.

12. The kit according to claim 1, wherein the first plus-sense single-stranded viral vector comprises a functional heterologous ORF in addition to the functional coat protein ORF and the second plus-sense single-stranded viral vector comprises a functional heterologous ORF in addition to the functional coat protein ORF.

13. The kit according to claim 1, wherein the first plus-sense single-stranded viral vector does not comprise a functional heterologous ORF in addition to the functional coat protein ORF and the second plus-sense single-stranded viral vector does not comprise a functional heterologous ORF in addition to the functional coat protein ORF.

14. The kit according to claim 1, wherein the first plus-sense single-stranded viral vector does not comprise a functional heterologous ORF in addition to the functional coat protein ORF or the second plus-sense single-stranded viral vector does not comprise a functional heterologous ORF in addition to the functional coat protein ORF.

15. The kit according to claim 4, wherein the at least one additional plus-sense single stranded RNA viral vector:

a) comprises the features of the first plus-sense single-stranded viral vector, and b) does not comprise an endogenous coat protein ORF, and c) comprises at least one functional heterologous ORF that is not present in the first or second plus-sense single-stranded viral vector.

16. The kit according to claim 4, wherein the at least one additional plus-sense single stranded RNA viral vector:

a) comprises the features of the first plus-sense single-stranded viral vector, and b) does not comprise an endogenous coat protein ORF, and c) comprises a functional heterologous coat protein ORF, and d) comprises at least one functional heterologous ORF that is not present in the first or second plus-sense single-stranded viral vector.

17. The kit according to claim 5, wherein the functional heterologous ORF(s) of the at least one additional plus-sense single stranded RNA viral vector is different from the functional heterologous ORF of the first or second plus-sense single-stranded viral vector.

18. The kit according to claim 5, wherein the at least one additional plus-sense single stranded RNA viral vector comprises a coat protein, a functional movement protein(s), and an RNA-dependent RNA Polymerase of the virus from which the second plus-sense single-stranded viral vector is derived.

19. The kit according to claim 4, wherein the at least additional plus-sense single stranded RNA viral vector comprises one functional heterologous ORF.

20. The kit according to claim 5, wherein the functional movement protein ORF of the virus from which the at least one additional plus-sense single-stranded viral vector is derived is completely deleted.

21. The kit according to claim 1, wherein a) said Potexvirus is potato virus x (PVX) or b) said Tobamovirus is tobacco mosaic virus (TMV).

22. The kit according to claim 4, wherein said Potexvirus is PVX.

23. The kit according to claim 4, wherein the coat protein ORF of the virus from which the at least one additional plus-sense single-stranded viral vector is derived is completely deleted in the at least one additional plus-sense single stranded RNA viral vector.

24. The kit according to claim 4, wherein the first plus-sense single stranded RNA viral vector is PVX, the second plus-sense single stranded RNA viral vector is TMV, and the at least one additional plus-sense single stranded RNA viral vector is PVX.

25. The kit according to claim 21, wherein a) said Potexvirus is PVX, and b) said Tobamovirus is TMV.

26. The mixture according to claim 6, wherein (i) the at least one third plus-sense single-stranded viral vector(s) comprise(s) at least one functional heterologous ORF, and (ii) the coat protein ORF of the virus from which the at least one third plus-sense single-stranded viral vector(s) is derived is completely deleted in the at least one third plus-sense single stranded RNA viral vector(s).

27. The mixture according to claim 6, wherein a) said Potexvirus is PVX, and/or b) said Tobamovirus is TMV.

28. The plant or plant cell according to claim 8, wherein (i) the at least one third plus-sense single-stranded viral vector(s) comprise(s) at least one functional heterologous ORF, and (ii) the coat protein ORF of the virus from which the at least one third plus-sense single-stranded viral vector(s) is derived is completely deleted in the at least one third plus-sense single stranded RNA viral vector(s).

29. The plant according to claim 8, wherein more than one plant cell in more than one tissue of the plant comprises the heterologous polypeptides encoded by the ORFs of at least two different third plus-sense single stranded RNA viral vector(s).

30. The plant or plant cell according to claim 8, wherein
a) said Potexvirus is PVX, and/or
b) said Tobamovirus is TMV.

31. The method of claim 10, wherein
(i) the at least one third plus-sense single-stranded viral vector(s) comprise(s) at least one functional heterologous ORF, and
(ii) the coat protein ORF of the virus from which the at least one third plus-sense single-stranded viral vector(s) is derived is completely deleted in the at least one third plus-sense single stranded RNA viral vector(s),
and further wherein
a) at least two third plus-sense single stranded RNA viral vectors are provided to at least one plant cell if the first plus-sense single stranded RNA viral vector and the second plus-sense single stranded RNA viral vector do not comprise a functional heterologous ORF, and
b) wherein at least two of the viral vectors according to (a) to (c) comprise different heterologous ORFs.

32. The method of claim 10, wherein
a) said Potexvirus is PVX, and/or
b) said Tobamovirus is TMV.

33. The method of claim 10, wherein the heterooligomeric polypeptide is an antibody or antibody fragment.

* * * * *

UNITED STATES PATENT AND TRADEMARK OFFICE
CERTIFICATE OF CORRECTION

PATENT NO. : 10,190,128 B2
APPLICATION NO. : 14/764112
DATED : January 29, 2019
INVENTOR(S) : Commandeur et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 313 days.

Signed and Sealed this
Thirtieth Day of July, 2019

Andrei Iancu
*Director of the United States Patent and Trademark Office*